(12) United States Patent
Vivenzio et al.

(10) Patent No.: US 11,547,291 B2
(45) Date of Patent: Jan. 10, 2023

(54) INTEGRATED ILLUMINATION ASSEMBLY FOR HANDHELD MEDICAL DEVICES

(71) Applicant: Welch Allyn, Inc., Skaneateles Falls, NY (US)

(72) Inventors: Robert L. Vivenzio, Auburn, NY (US); Raymond A. Lia, Auburn, NY (US); Chris R. Roberts, Skaneateles, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 129 days.

(21) Appl. No.: 16/800,578

(22) Filed: Feb. 25, 2020

(65) Prior Publication Data
US 2020/0337541 A1    Oct. 29, 2020

Related U.S. Application Data

(60) Provisional application No. 62/810,976, filed on Feb. 27, 2019.

(51) Int. Cl.
| | |
|---|---|
| *A61B 1/303* | (2006.01) |
| *A61B 1/06* | (2006.01) |
| *A61B 1/32* | (2006.01) |
| *A61B 1/00* | (2006.01) |
| *A61B 1/31* | (2006.01) |

(Continued)

(52) U.S. Cl.
CPC .......... *A61B 1/303* (2013.01); *A61B 1/00032* (2013.01); *A61B 1/00066* (2013.01); *A61B 1/0669* (2013.01); *A61B 1/0684* (2013.01); *A61B 1/07* (2013.01); *A61B 1/267* (2013.01); *A61B 1/31* (2013.01); *A61B 1/32* (2013.01)

(58) Field of Classification Search
CPC ......... A61B 1/0684; A61B 1/303; A61B 1/32; A61B 1/31; A61B 1/0669; A61B 1/0661–1/0692
See application file for complete search history.

(56) References Cited

U.S. PATENT DOCUMENTS

| | | | |
|---|---|---|---|
| 7,081,090 B2 | 7/2006 | Strong et al. | |
| 8,157,728 B2 * | 4/2012 | Danna ...................... | A61B 1/06 600/223 |

(Continued)

FOREIGN PATENT DOCUMENTS

WO    WO-2006107878 A2 *  10/2006  ......... A61B 1/00105

*Primary Examiner* — Julianna N Harvey
(74) *Attorney, Agent, or Firm* — Barclay Damon LLP

(57) ABSTRACT

A medical device includes a handle portion downwardly extending from an examination portion. The handle portion has opposing upper and lower open ends and a through cavity extending therebetween. An illumination assembly mounted within the open upper end of cavity includes a housing, at least one battery disposed within the housing, and an LED disposed at the distal end of an arm extending from the housing. The housing is mounted through the open upper end of the through cavity. According to at least one version, the at least one battery can be removed without removing the housing from the handle portion. The extending arm is supported by the examination portion and configured to provide illumination to a medical target. The medical device can include a vaginal speculum, sigmoidoscope, laryngoscope, anoscope, or other hand-held medical device.

15 Claims, 21 Drawing Sheets

(51) Int. Cl.
  *A61B 1/267* (2006.01)
  *A61B 1/07* (2006.01)

(56) References Cited

U.S. PATENT DOCUMENTS

| | | | |
|---|---|---|---|
| 8,821,395 B2 | 9/2014 | McMahon et al. | |
| 2007/0230164 A1* | 10/2007 | Vivenzio | A61B 1/32 362/109 |
| 2009/0082695 A1* | 3/2009 | Whitehead | A61B 1/303 600/562 |
| 2009/0097236 A1* | 4/2009 | Miller | A61B 1/32 362/119 |
| 2009/0198108 A1* | 8/2009 | Chen | A61B 1/00103 600/220 |
| 2009/0312610 A1* | 12/2009 | Buchok | A61B 1/32 600/205 |
| 2014/0309499 A1* | 10/2014 | Swift | A61B 1/0684 600/214 |
| 2016/0038012 A1* | 2/2016 | McMahon | A61B 1/0669 600/210 |
| 2017/0181615 A1* | 6/2017 | Vella | A61B 1/06 |
| 2017/0181616 A1* | 6/2017 | Vella | A61B 1/303 |
| 2019/0117058 A1* | 4/2019 | Clark | A61B 1/0684 |

\* cited by examiner

INTEGRATED ILLUMINATION ASSEMBLY FOR HANDHELD MEDICAL DEVICES

CROSS REFERENCE TO RELATED APPLICATION

This application claims priority to U.S. Ser. No. 62/810,976, filed Feb. 27, 2019 under relevant portions of 35 U.S.C. §§ 119 and 120, the entire contents of which are incorporated by reference.

TECHNICAL FIELD

The application is generally directed to the field of diagnostic medicine and more specifically to handheld medical devices or instruments equipped with an integrated illumination assembly.

BRIEF BACKGROUND

Attempts have been made to improve the design of vaginal speculums, which are used for examining the cervix of female patients. Known specula for this purpose have been made in accordance with a number of designs. For example, a Graves speculum is typically defined by a top blade member and a bottom blade member that are coupled to each other and whose relative spacing can be adjusted by an articulation or moving mechanism for purposes of dilating the female patient. A distal blade end of the speculum extends to the patient and the medical target is viewed through an aperture which is formed between the top and bottom blade members at the proximal end of the speculum. An illumination assembly disposed within the speculum includes a light source that facilitates viewing of the intended target.

In prior versions, illumination assemblies were tethered to the speculum and coupled to a remote power source as described by Strong et al. (U.S. Pat. No. 7,081,090 B2). These illumination assemblies include a housing retained in a receiving cavity formed in a handle portion of the speculum. The output of a contained incandescent lamp is coupled to the proximal end of a curved light transmissive pipe that directs the output from the proximal end of the curved light pipe to a distal end and to the intended medical target. The housing of the illumination assembly is tethered by a cord to a remote power source and an in-line switch allows a user to selectively energize the contained incandescent lamp.

In accordance with more recent developments, a compact illumination assembly has been introduced that replaces the previously described tethered version. This design, which is described in U.S. Pat. No. 8,821,395, includes an LED disposed within a housing along with at least one rechargeable battery. The housing is disposed within a cavity formed in the handle portion of the speculum and like the prior described tethered illumination assembly, the emitted output of the retained LED is optically coupled to the proximal end of a curved light transmissive pipe provided at the closed end of the handle portion for direction to the medical target.

Still other designs have since been developed that include an integrated illumination assembly fixedly secured to the handle portion or other feature of the speculum. The housing of the illumination assembly retains a light source, as well as a compact power supply. A releasable tab portion extends from the housing. When the releasable tab portion is pulled by the user, the contained light source is automatically energized. The speculum and illumination assembly are designed in this case for use as a single use or single patient device.

For specula and illumination assemblies that are deemed to be disposable (single patient or single use), and due to existing regulations in the United States and a number of other countries, the contained batteries must be removed before recycling. Depending on the location of the illumination assembly within the vaginal speculum, removal of the contained batteries can be difficult and time intensive.

Accordingly, there is a pervasive and ongoing need in the field to improve the efficiency and structural integrity of single use or single patient vaginal specula. There is also a need to develop a speculum with a portable illumination assembly that enables recyclability, while further permitting the contained batteries to be easily removed while the illumination assembly is still retained on or within the speculum.

There is a further present and ongoing need in hospitals and other medical care facilities to prevent the spread of diseases and contaminants through the use of single use or single patient medical devices for purposes of diagnosis and examination, as opposed to the various risks and overall inconvenience involved with the cleaning and reuse of dedicated medical devices between patients.

BRIEF DESCRIPTION

Therefore and according to one aspect of the present invention, there is provided a vaginal speculum comprising a first blade and a second blade, each of the first and second blades having a trough-shaped blade section. A handle portion extends downwardly from the second blade that permits the speculum to be handheld. An illumination assembly includes a housing that retains at least one battery, as well as a light source disposed within a curved arm extending from the housing. The housing is mounted into the upper open end of a through cavity of the handle portion with the curved arm being supported by the bottom blade. The curved arm is sized and configured to position an LED at the distal end of the curved arm within the trough-shaped blade section of the second blade.

According to at least one embodiment, a plurality of batteries are releasably disposed within the housing of the illumination assembly. The housing can include a hinged cover in which the batteries can be supported by an integral feature provided in the housing interior. The hinged cover can be opened, even while the illumination assembly is supported within the speculum, to effect release of the batteries following use. According to one embodiment, a tool can access and open the hinged cover from the lower open end of the through cavity. According to another embodiment, a supporting feature of the contained batteries can be made part of a battery release member, the latter having a portion that extends from the housing. Following use of the speculum, an extending portion of the releasable member can be accessed from the open lower end of the handle portion in order to effect battery release prior to recycling the speculum.

According to at least one embodiment, a releasable tab member can also extend from the housing of the illumination assembly, the tab member being configured to energize the contained light source when pulled from the housing. In at least one version, the battery release member includes at least one feature that supports the releasable tab member such that the releasable tab member can be pulled from the housing in order to energize the contained light source and permit an examination to be conducted. Following use, the extending portion of the battery release member can be pulled from the housing to release the contained batteries prior to recycling the vaginal speculum, including the mounted illumination assembly.

Alternatively, the upper end of the housing of the illumination assembly can be accessed from the upper open end of the through cavity of the speculum. In one version, the upper end of the housing can include a recess or other gripping area to enable the housing to be extracted. In at least one embodiment, the housing or the through cavity can include a set of frangible tabs or similar supporting features. Removal of the housing breaks or disables the frangible tabs and prevents the illumination assembly and/or the speculum from being reused.

According to at least one version, the curved arm of the illumination assembly is integral to the housing with at least one LED being disposed at the distal end of the arm. A recess formed in the bottom blade member is sized and shaped to accommodate a portion of the curved arm and promote illumination toward the distal end of the speculum. Unlike previously known light pipes, there is no need to provide a material that promotes internal reflection of emitted light, since the LED is already disposed at the distal end of the curved arm.

According to another aspect, there is provided an illumination assembly for use in a medical device. The illumination assembly comprises a housing having an upper end, an opposing lower end and a curved arm extending from the housing. At least one battery is disposed within the housing and an LED is mounted at a distal end of the curved arm. The housing is sized and shaped to be fitted within the open upper end of a handle portion of the medical device, with the upper end of the housing having a width dimension that is larger than the width dimension of the open upper end of the handle portion. Preferably, the illumination assembly can be fixedly attached or integrated as part of the medical device with the illumination assembly and the medical device both being intended for single patient or single use. The medical device is preferably a hand-held diagnostic instrument such as, but not limited to a vaginal speculum, colposcope, sigmoidoscope, laryngoscope, rhinoscope, anoscope, and skin measuring microscope. The medical device includes an examination portion, such as a blade, into which the curved arm of the housing extends, enabling the supported LED to direct light to a medical target.

According to at least one version, the housing of the illumination assembly includes a hinged cover. In at least one embodiment, an extending battery release member enables the at least one battery to be removed from the housing without having to first remove the illumination assembly from the handle portion of the medical device. According to at least one embodiment, the medical device can include at least one guide positioned and configured to assist in the transmission of light from the illumination assembly to the medical target of interest. The herein described illumination assembly is configured and designed to be fitted into a plurality of different medical devices, thereby creating a suite of recyclable products that can be configured for single or single patient use.

According to yet another aspect, there is provided a method for examining a patient using a recyclable medical device. The medical device includes an examination section and a handle portion downwardly extending from the examination section. An illumination assembly is disposed within the upper open end of a through cavity of the handle portion. According to the method, a releasable tab portion can be pulled from the open lower end of the handle portion to cause energization of an LED disposed at a distal end of an extending arm of the illumination assembly, with the arm being supported by the examination section. Following an examination procedure, one end of a battery release member can be engaged from an lower open end of the cavity, causing at least one battery to be withdrawn from the illuminator assembly and without first removing the illumination assembly from the device. In at least one version, the battery release member also retains the releasable tab portion.

Alternatively, the illumination assembly can be removed directly from the opened upper end of the handle portion. In at least one version, a set of frangible tabs or similar support features can be provided on the illumination assembly housing and/or within the receiving slot of the handle portion of the medical device. The removal of the illumination assembly breaks or otherwise disables the tabs and renders them non-functional, thus guaranteeing that the illumination assembly and/or the medical device cannot be reused.

Preferably, all of the components of the device are disposable, enabling the illumination assembly and medical device to be recycled all at one time.

The inclusion of the open ended cavity in the upper end of the handle portion, as well as the frangible tabs simplifies alignment of the illumination assembly during manufacture of the medical device. That is, no special alignment features are required between the handle portion and the illuminator assembly.

The herein described improvements permit the handle portion of a sigmoidoscope, anoscope, laryngoscope, vaginal speculum or other hand-held medical instrument to be made smaller and more compact. Though less material is required, structural integrity of the medical device is maintained and in fact improved for its intended use.

Another advantage provided by the herein described device is that the batteries can be easily removed following use, easing the recycling process for the medical device, including contained illumination assembly.

In addition, having the LED disposed at the distal end of the extending arm enables the medical device and illumination assembly to be made from materials that do not necessarily require or promote light transmission.

Consequently, the herein described speculum or other medical device can be molded using lower strength plastic materials, such as polypropylene. This provides yet another advantage in that as a recyclable material, polypropylene is clean burning. In addition, materials that were required for light transmission were inherently brittle. The materials that can be used in the herein described speculum or other hand-held medical device are significantly less brittle and have poor light transmissive capabilities. However and because light transmissive qualities are not critical due to direct illumination, these materials can now be considered for use, which aids in manufacturability and product life.

According to yet another advantage, a suite of single use or single patient medical devices can be commonly equipped with an integrated illumination assembly as described herein, reducing the risk of contamination or disease associated with the cleaning or lack of cleaning of reusable devices.

These and other features and advantages will be readily apparent to the reader from the following Detailed Description, which should be read in conjunction with the accompanying drawings.

DETAILED DESCRIPTION

The following relates to an illumination assembly made in accordance with various embodiments that can be configured for use in a plurality of recyclable single use or single patient medical devices or instruments, particularly those devices with a handle portion that permits one-handed operation. A detailed description of an illumination assembly as integrated into a specific medical device, namely a disposable and recyclable vaginal speculum is first discussed. However, it will be readily apparent that the inventive aspects described herein are similarly applicable for incorporation into a number of other medical devices. In addition and throughout the course of discussion, several terms are used in order to provide a suitable frame of reference with regard to the accompanying drawings. These terms, which include "first", "second", "top", "bottom", "inner", "outer", "above", "below", "distal" and "proximal" among others, are not intended to be overly limiting of the invention, except where so specifically indicated. In addition, the accompanying drawings are intended to depict salient features of the present invention. In this regard, the drawings are not necessarily to scale and should not be relied upon for purposes of scaling or sizing.

Figures 1A, 1B:
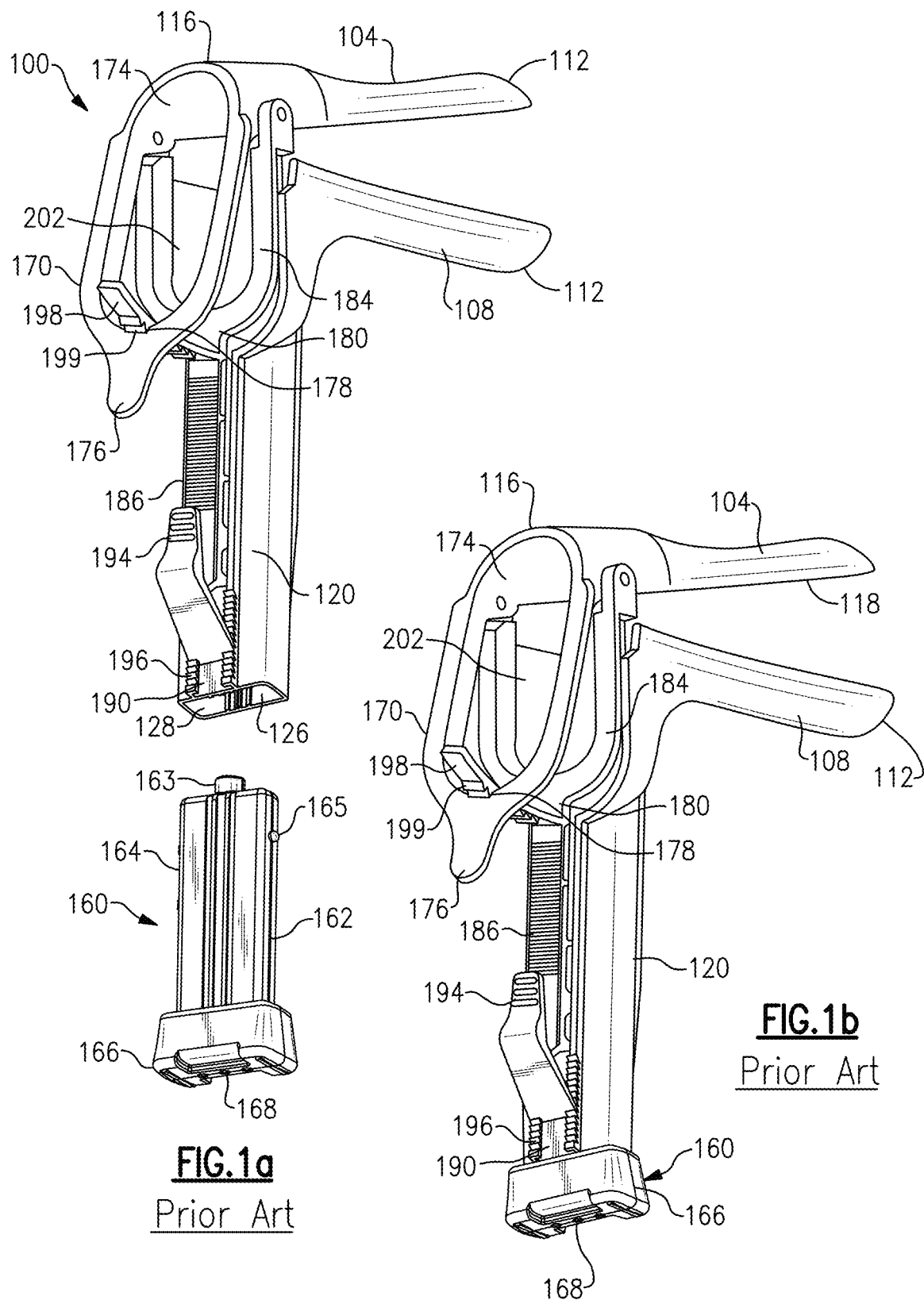
FIG. 1(a) is a rear perspective assembly view of a known vaginal speculum, including a portable illuminator.
FIG. 1(b) is the rear perspective view of the vaginal speculum of FIG. 1(a), with the portable illuminator assembled.
Figure 1C:
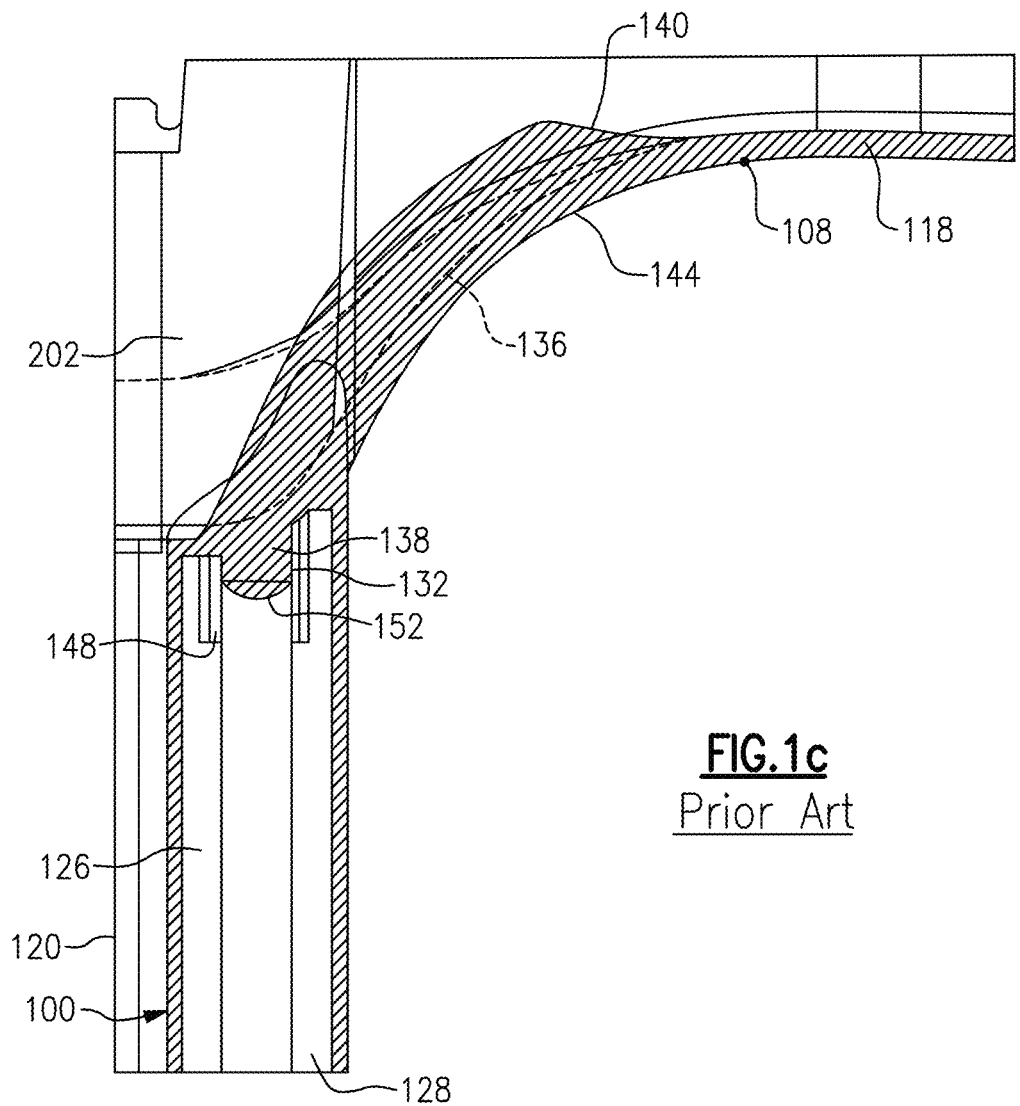
FIG. 1(c) is a side elevational view, taken in section, of the handle portion and a section of the lower blade member of the vaginal speculum of FIGS. 1(a) and 1(b)

For purposes of background and with reference to FIGS. 1(a)-1(c), there is shown a known medical device and more specifically, a vaginal speculum 100. The vaginal speculum 100 is defined by a first or top blade member 104, as well as a second or bottom blade member 108. Each of the blade members 104, 108 include a distal end 112 having a trough-shaped blade portion 118, as well as an opposing proximal end 116. The top and bottom blade members 104, 108 are coupled together by means of an articulation or moving mechanism, described in greater detail below.

A handle portion 120 extends downwardly from the proximal end 116 of the bottom blade member 108. The handle portion 120 is defined by a shape that permits gripping and use of the speculum 100 by a single hand of the user. The handle portion 120 is fully enclosed with the exception of an open lower end 128. An enclosed receiving cavity 126 extends from the open lower end 128 to a closed upper end 132 of the handle portion 120. A curved light pipe 136 extending from the closed upper end 132 of the handle portion 120 is defined by opposing proximal and distal ends 138, 140, respectively. The light pipe 136 extends along a necked portion 144 of the bottom blade member 108 defined between the handle portion 120 and the trough-shaped blade portion 118 of the bottom blade member 108. A coupling and aligning feature is provided at the closed upper end 132 of the enclosed receiving cavity 126, which includes centering fingers 148 disposed at the closed upper end 132 that are aligned with a lens 152 formed at the proximal end 138 of the light pipe 136. As noted, the light pipe 136 extends in a curved configuration along the necked portion 144, as shown in FIG. 1(c), and is made from an optically clear light transmissive material, such as an acrylic, that promotes internal reflection.

A known portable illumination assembly 160 is advanced within the open lower end 128 of the enclosed receiving cavity 126 of handle portion 120. The illumination assembly 160 is defined by a housing 162 having an upper portion 164 that retains a light source (not shown) adjacent an upper end 163 and a lower portion 166. The lower portion 166 includes at least one charging contact 168 that enables a contained battery (not shown) to be recharged. The upper portion 164 of the housing 162 is sized to be fitted within the receiving cavity 126 of the handle portion 120 through the open lower end 128. The upper portion 164 includes an exterior slide switch 165 that causes the contained light source to be energized when the illumination assembly 160 is sufficiently advanced into the enclosed receiving cavity 126. The illumination assembly 160 is further advanced until the upper end 163 of the housing 162 is aligned within the centering fingers 148 and the light source of the illumination assembly 160 is aligned with the lens 152 and the proximal end 138 of the curved light pipe 136. Further axial movement is prevented by the lower portion 166 of the housing 162, which is larger in width than the open lower end 128 of the receiving cavity 126. Further details relating to the illumination assembly 160 are described in U.S. Pat. No. 8,821,395, which is incorporated in its entirety. When the illumination assembly 160 is powered and the contained light source is energized, such as by the exterior slide switch 165, the emitted light is directed through the lens 152 and is transmitted by internal reflection through the curved light pipe 136.

Referring to FIGS. 1(a)-1(c), a moving or articulation mechanism is provided to enable the spacing of the top and bottom blade members 104, 108 to be selectively adjusted for purposes of adequately dilating a patient. This moving mechanism includes a lever portion 170 that is attached to the proximal end 116 of the top blade member 104 and a yoke 180 that is mounted to the proximal end 116 of the bottom blade member 108 and the handle portion 120. The lever portion 170 is integral to the top blade member 104 and extends downwardly relative to the remainder of the top blade member 104 at a reflexed angle. The lever portion 170 includes a viewing aperture 174, as well as a lower tab 176 disposed beneath the viewing aperture 174, the lower tab 176 having a slot 178.

The yoke 180 includes a yoke portion 182 defined by a pair of upwardly extending spaced arms 184, the upper ends of the arms 184 being pivotally attached to the proximal end 116 of the top blade member 104. The yoke 180 further includes a slide member 186 downwardly extending from the lower end of the yoke portion 182. The slide member 186 is movably disposed within a vertical slot 190 formed on a rear facing side of the handle portion 120. The slide member 186 further includes a lower locking member 194 sized and configured to engage a set of spaced teeth 196 formed on opposing sides of the vertical slot 190, as well as an arcuate pawl arm 198 between the yoke portion 182 and the slide member 186 that extends proximally away from the proximal end 116 of the speculum 100. The arcuate pawl arm 198 is curved and includes a set of spaced ratchet teeth 199 that are configured to engage the slot 178 formed on the lower tab 176 of the lever portion 170. The proximal end 116 of the lower blade member 108 is further defined by a recessed portion 202 that is sized to retain the yoke portion 182 and permit viewing through the viewing aperture 174.

In use, the moving mechanism enables the spacing of the top and bottom blade members 104, 108 to be adjusted. The bottom blade member 108 is fixed while the position of the top blade member 104 can be adjusted by engaging the slide member 186 and elevating or lowering the yoke 180 against the pivotally attached upper blade member 104. The angular position between the top and bottom blade members 104, 108 can be further adjusted by pushing upwardly against the arcuate pawl arm 198 and varying the position of the arm 198 relative to the slot 178 of the lower tab 176 of the lever portion 170.

The illumination assembly 160 is disposed within the enclosed receiving cavity 126 of the handle portion 120 in which the upper end 163 of the housing 162 is aligned with the lens 152 via the centering fingers 148. Illumination is directed from the light source (not shown) through the lens 152 and the proximal end 138 of the curved light pipe 136 with the transmitted light being emitted from the distal end 140 of the curved light pipe 136 toward the distal end 112 of the speculum 100 and the medical target of interest. According to one version, the distal end 140 of the curved light pipe 136 is angled to prevent the incidence of back reflection (glare) relative to the user.

With the foregoing background, a vaginal speculum 1000 made in accordance with an exemplary embodiment and having an integrated illumination assembly 1100 is shown in FIGS. 2-10. First and referring to FIGS. 2, 4(a) and 4(b), the speculum 1000 is defined by an upper or first blade member 1004 and a lower or second blade member 1008. Each of the upper and lower blade members 1004, 1008 is further defined by a distal end 1012 having a trough-shaped blade portion 1016, as well as an opposing proximal end 1018. The speculum 1000 further includes a handle portion 1020 downwardly extending from the proximal end 1018 of the lower blade member 1008. The handle portion 1020 is sized to enable the speculum 1000 to be held in a single hand of the user/caregiver.

Figure 2:
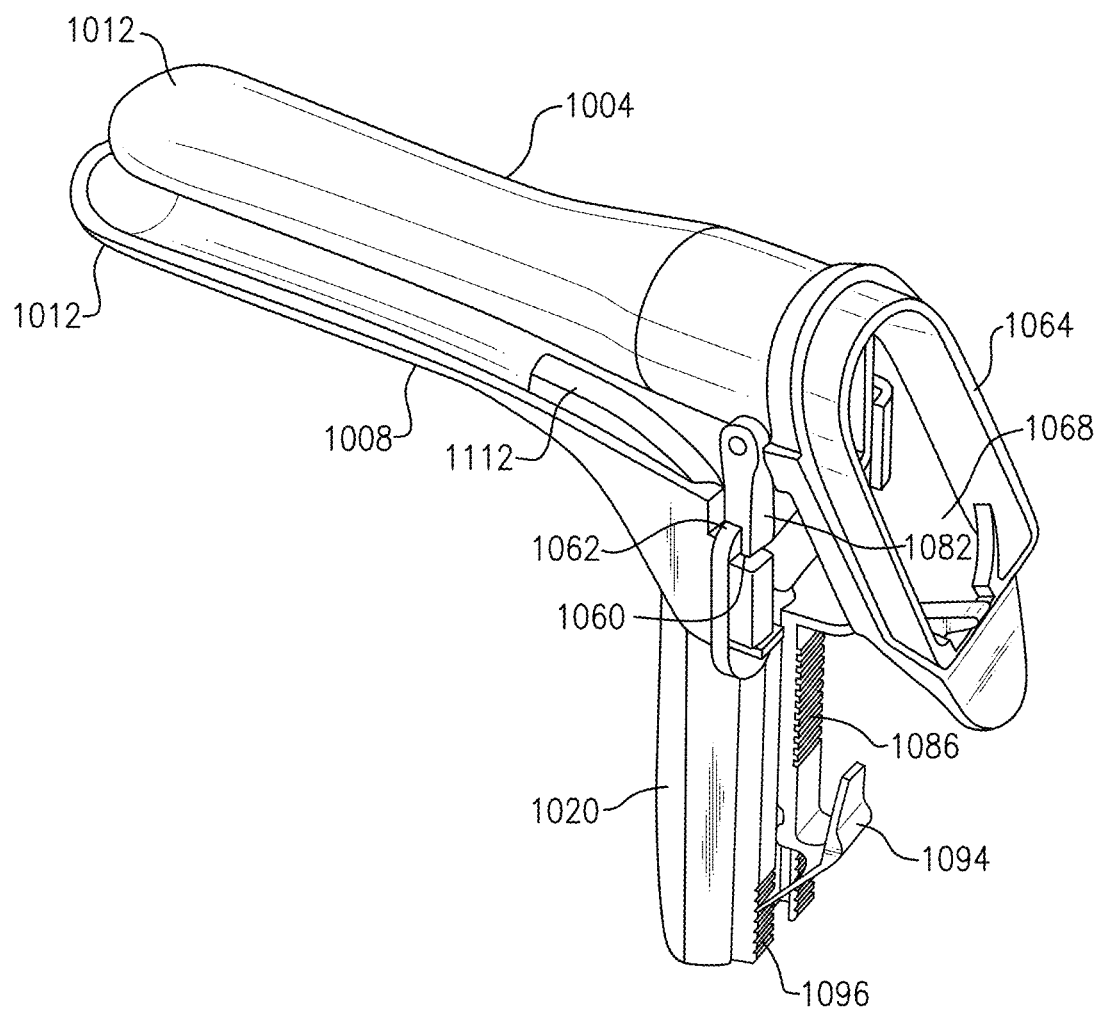
FIG. 2 is a rear perspective view of a vaginal speculum made in accordance with aspects of the invention.
Figure 4A:
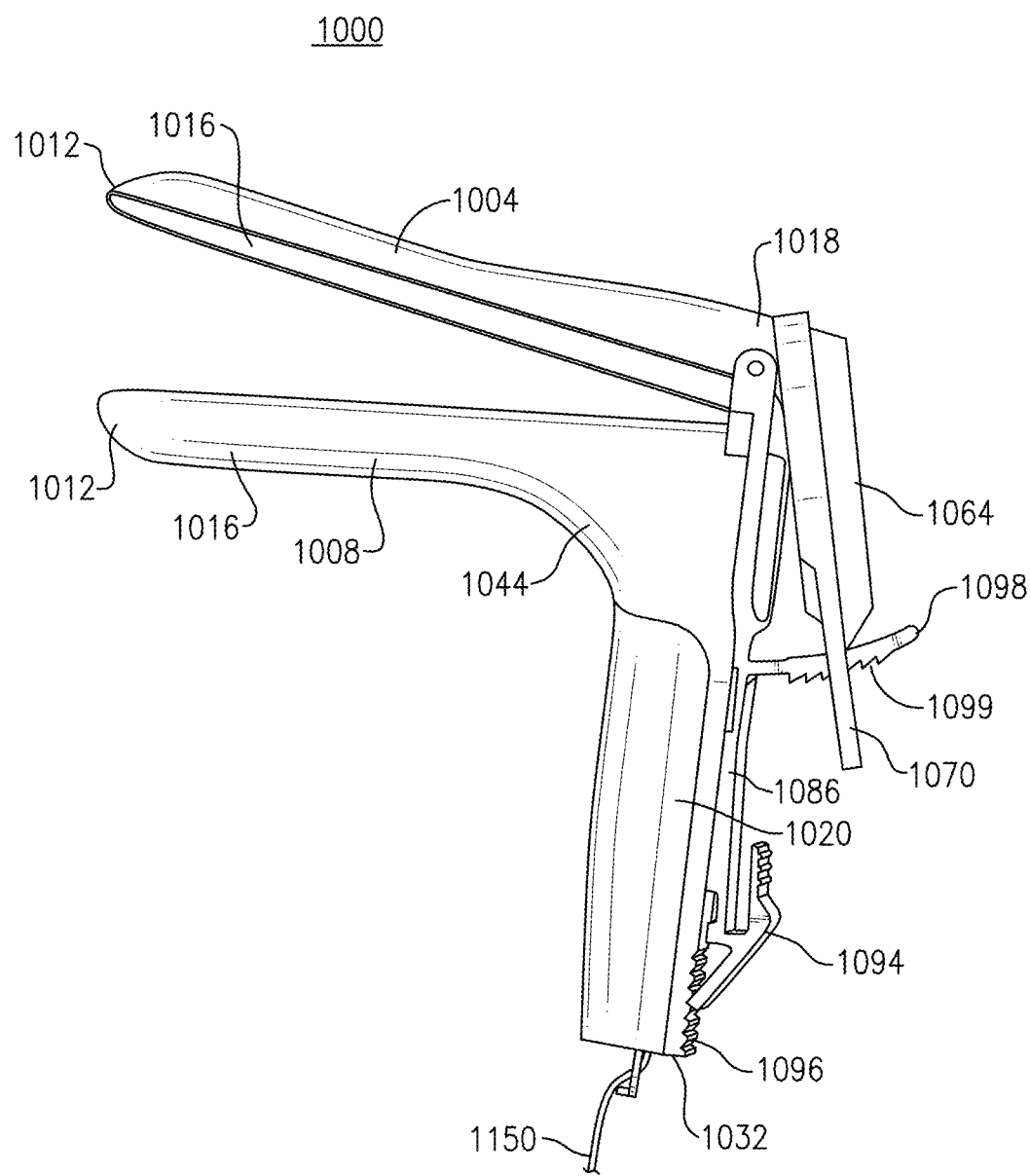
FIG. 4(a) is a side elevation view of the vaginal speculum of FIGS. 2 and 3, including an integrated illumination assembly.
Figure 4B:
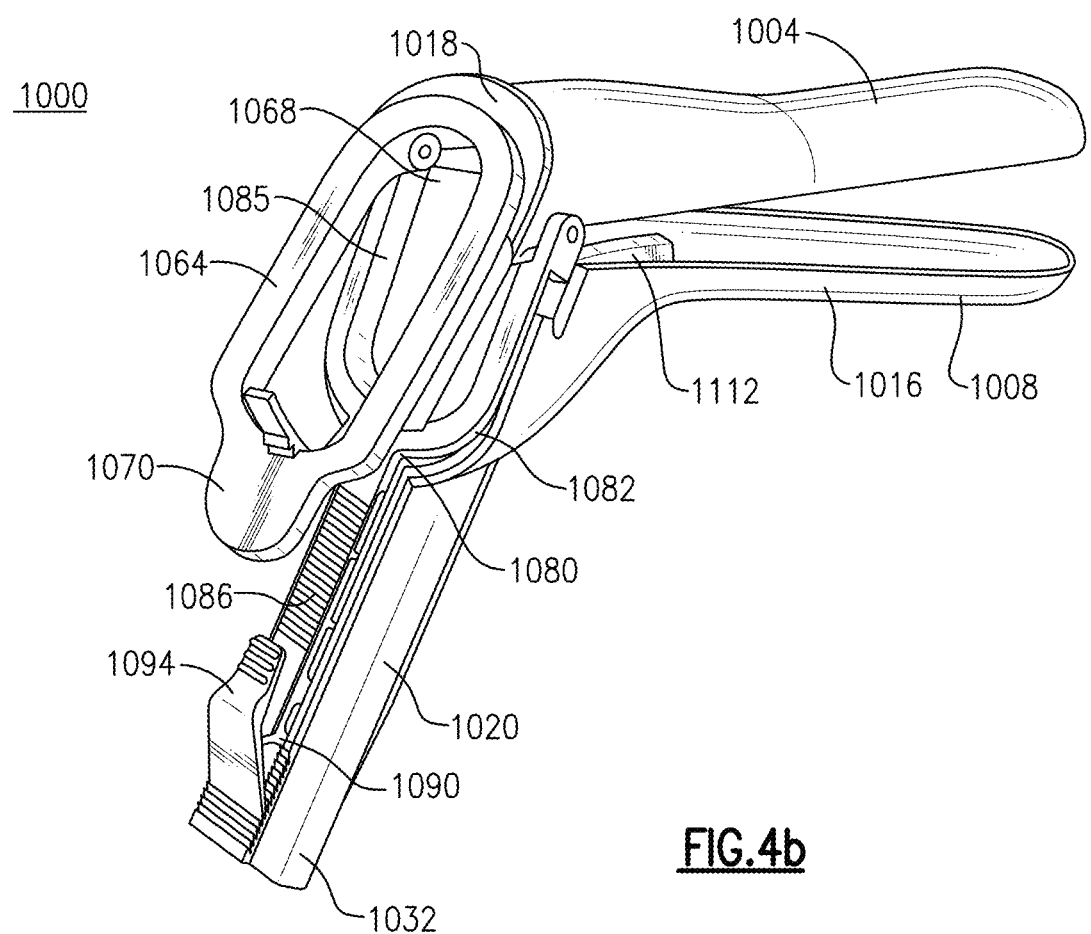
FIG. 4(b) is a rear perspective view of the vaginal speculum of FIGS. 2-4(a)

Like the prior described version in FIGS. 1(a)-1(c), the vaginal speculum 1000 includes a moving or articulation mechanism that enables the spacing of the upper and lower blade members 1004, 1008 to be selectively adjusted for purposes of adequately dilating a patient. As shown in FIGS. 2, 4(a) and 4(b), this moving mechanism includes a lever portion 1064 that is attached to the proximal end 1018 of the upper blade member 1004 and a yoke 1080 mounted to the proximal end 1018 of the lower blade member 1008 and the handle portion 1020. The lever portion 1064 extends downwardly relative to the upper blade member 1004 at a reflexed angle and includes a viewing aperture 1068, as well as a lower tab 1070 disposed beneath the viewing aperture 1068, the lower tab 1070 having a slot 1074. Preferably, the lever portion 1064 is integral with the housing 1004. According to this embodiment, the upper and lower blade members 1004, 1008 and the handle portion 1020 are each made from a lightweight plastic material, which is preferably moldable. Examples of suitable materials that further permit recyclability of the speculum 1000 include polyethylene, polyamide, and acrylic.

The yoke 1080 includes a yoke portion 1084 defined by a pair of upwardly extending spaced arms 1085, the upper ends of the extending arms 1085 being pivotally attached to the proximal end 1018 of the upper blade member 1004. The yoke 1080 further includes a slide member 1086 downwardly extending from the lower end of the yoke portion 1084. The slide member 1086 is movably disposed within a vertical slot 1090 formed on a rear facing side of the handle portion 1020. The slide member 1086 further includes a lower locking member 1094 sized and configured to engage a set of spaced teeth 1096 formed on opposing sides of the vertical slot 1090. An arcuate pawl arm 1098, disposed between the yoke portion 1084 and the slide member 1086, extends proximally away from the proximal end 1018 of the speculum 1000. The arcuate pawl arm 1098, which is curved, includes a set of ratchet teeth 1099 that engage the slot 1074 formed on the lower tab 1070 of the lever portion 1064.

As in the prior described version of FIGS. 1(a)-1(c), the proximal end 1018 of the lower blade member 1008 includes a recessed portion 1056 that is sized to retain the yoke section 1084 and permit viewing through the viewing aperture 1068. To provide additional stability and as shown in FIGS. 2, 3, 6 and 8, the recessed portion 1056 at the proximal end 1018 of the lower blade member 1008 is further defined by a pair of channels 1060 that include guiding features such as shoulders 1062, each suitably sized and configured to engage, axially guide and stabilize the upwardly extending arms 1085 of the yoke portion 1084.

In use, the moving mechanism enables the spacing of the upper and lower blade members 1004, 1008 to be selectively adjusted. The lower blade member 1008 is fixed while the position of the upper blade member 1004 can be adjusted by engaging the locking member 1094 and pushing or pulling the slide member 1086 in the vertical slot 1090. Movement of the slide member 1086 elevates or lowers the yoke portion 1082, as guided by the channels 1060 and shoulders 1062, against the pivotally attached upper blade member 1004. The angular position between the upper and lower blade members 1004, 1008 can be further adjusted by pushing the arcuate pawl arm 1098 upwardly relative to the slot 1074 formed in the lower tab 1070 of the lever portion 1064 and shifting the position of the lever portion 1064 relative to the set of ratchet teeth 1099 of the arcuate pawl arm 1098.

Figure 3:
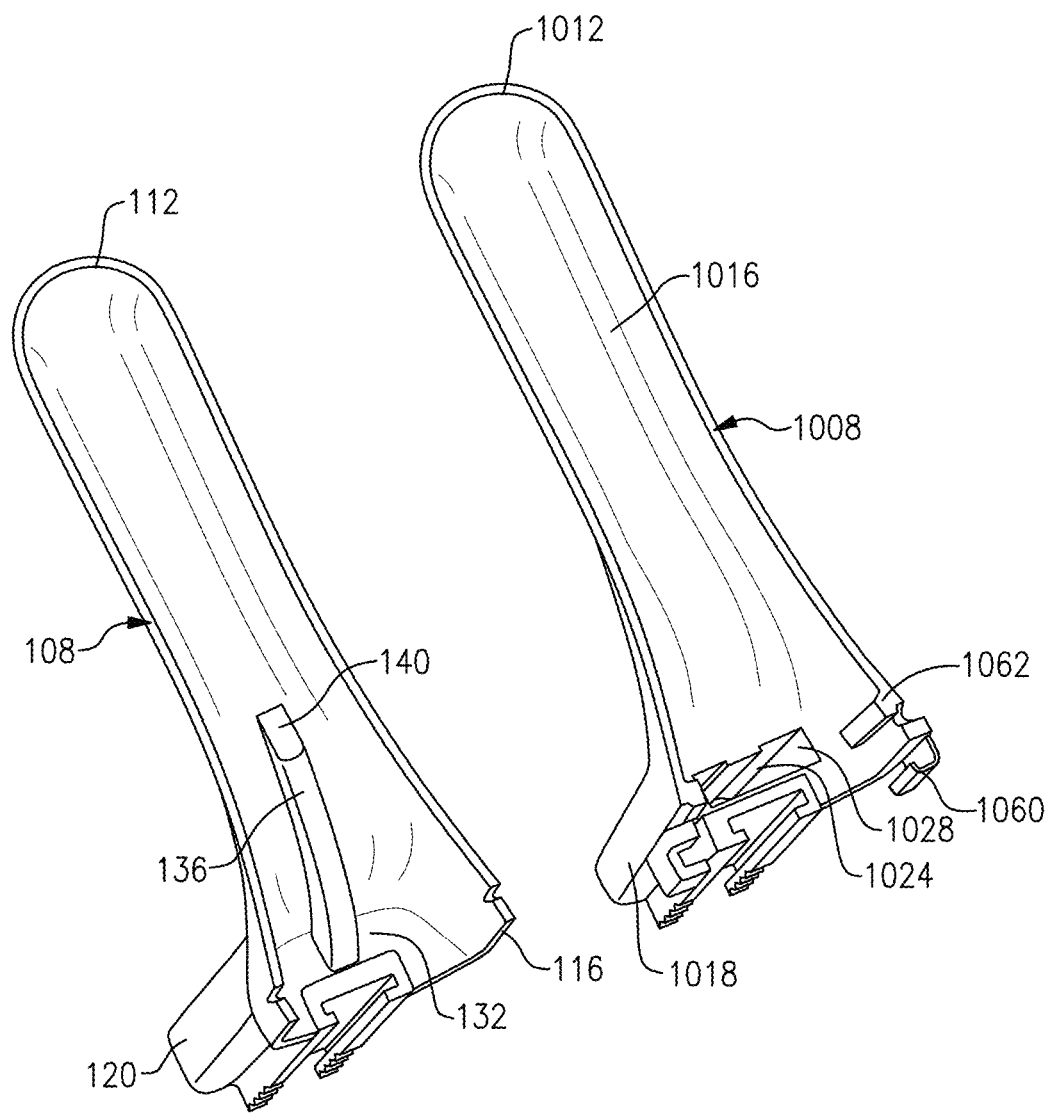
FIG. 3 depicts a side by side comparison between a lower blade member of the known speculum of FIGS. 1(a)-1(c) and the speculum of FIG. 2.
Figure 8:
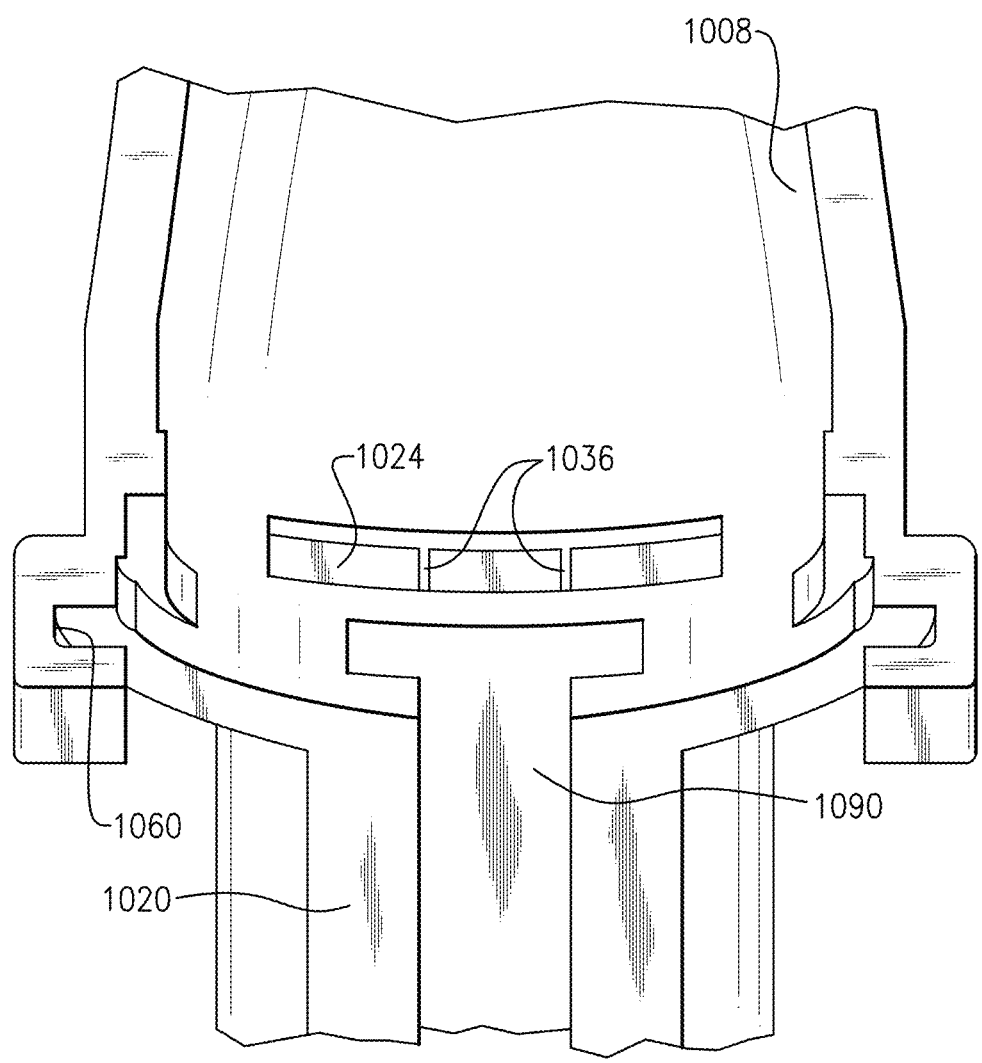
FIG. 8 is a top facing view of the proximal end of the lower blade member and handle portion of the speculum of FIGS. 2-7.

According to this embodiment and as shown in FIGS. 3 and 8, the handle portion 1020 is defined by an axial cavity 1024 that is fully enclosed with the exception of the open and opposing upper and lower ends 1028, 1032. The interior of the enclosed cavity 1024 can include at least one guide rail. According to this embodiment, a pair of guide rails 1036 (only one pair being shown) provided on opposing sides of the enclosed cavity 1024 extends over substantially the entire axial length of the enclosed cavity 1024. The number and spacing of these latter features can be suitably varied for use in aligning and retaining an illuminator assembly 1100.

Figure 5A:
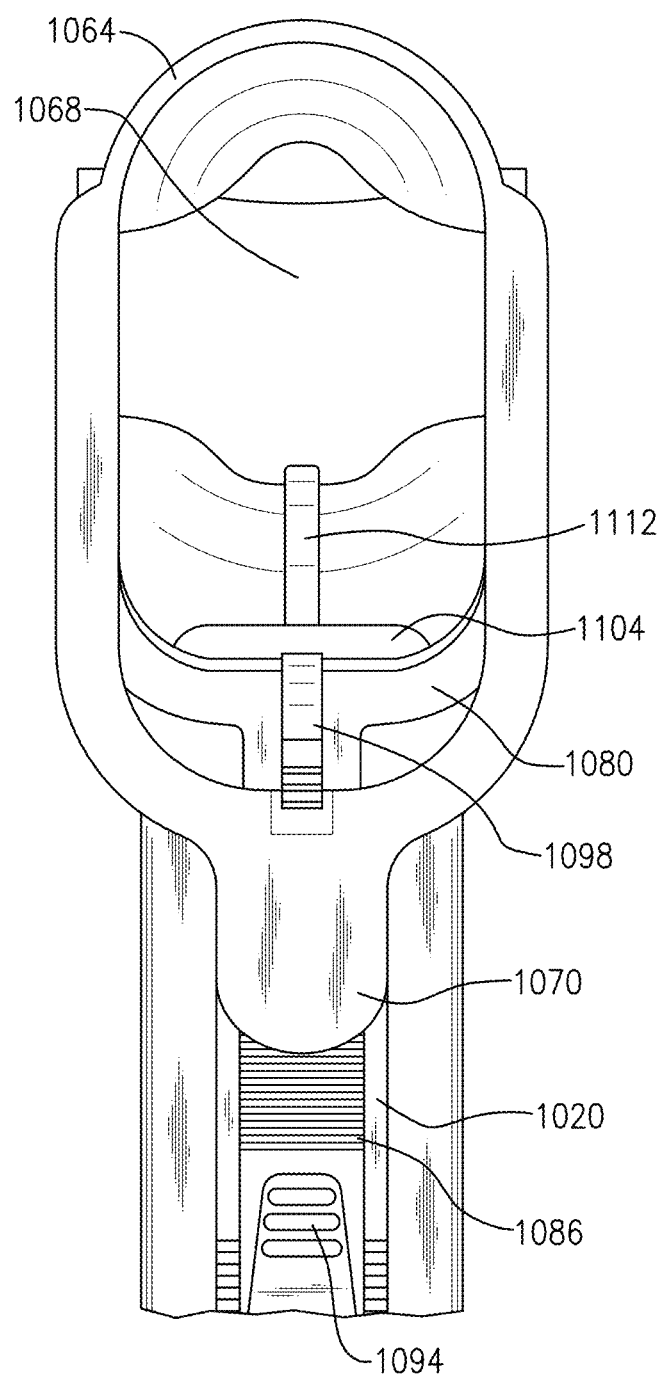
FIG. 5(a) is a rear facing view of the vaginal speculum of FIGS. 2-4(b)
Figure 5B:
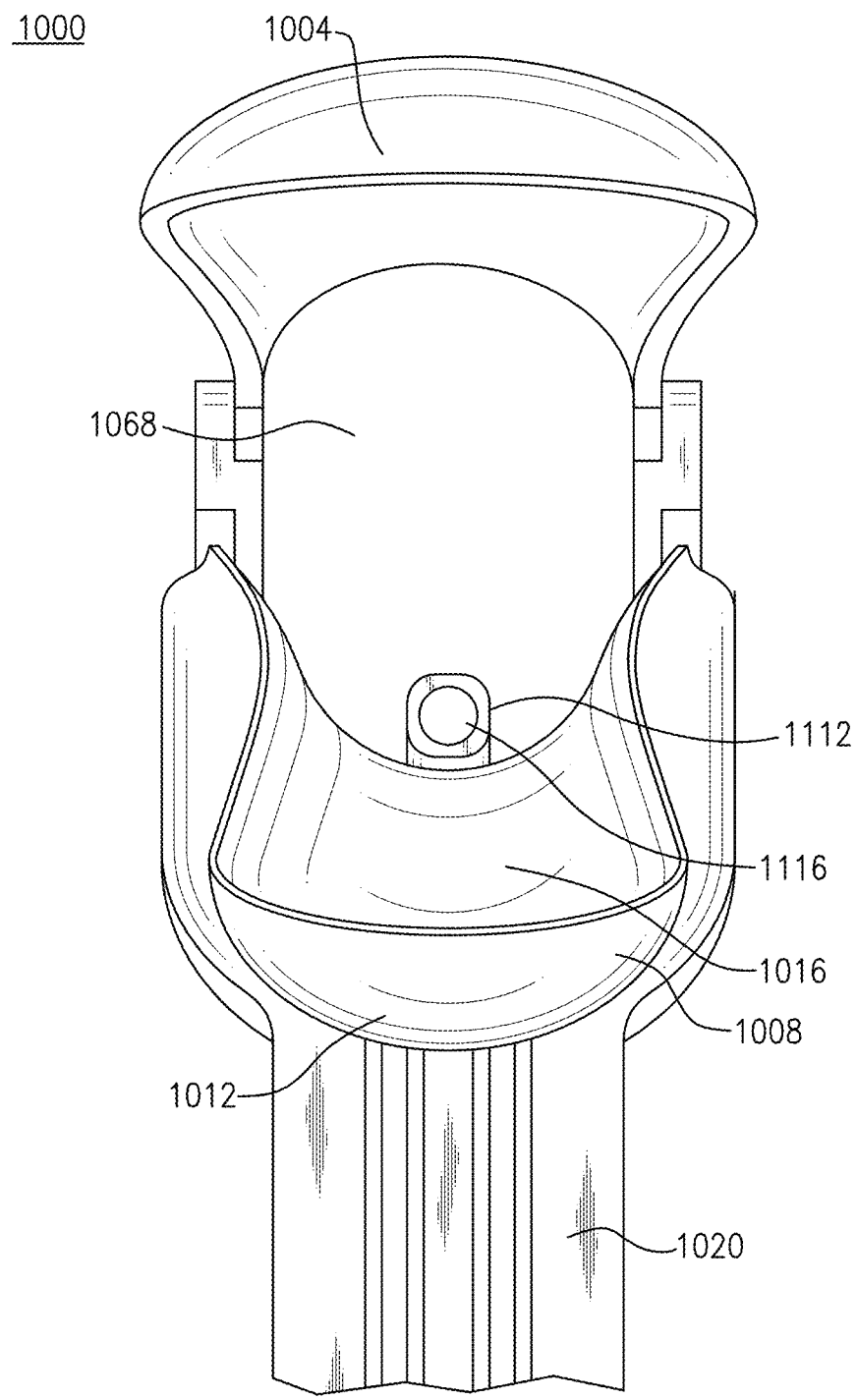
FIG. 5(b) is a front facing view of the vaginal speculum of FIGS. 2-5(a)
Figure 6:
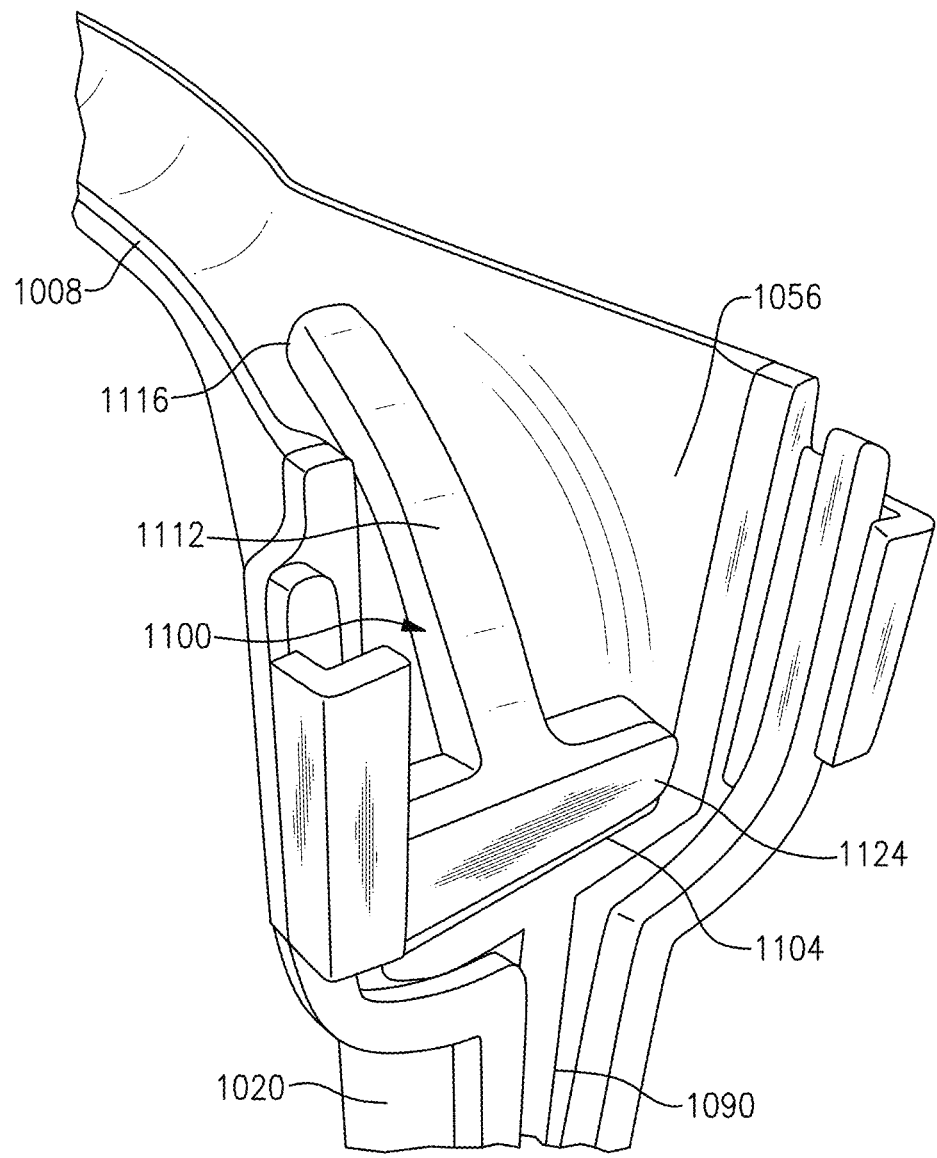
FIG. 6 is a rear perspective enlarged view of the lower blade member of the speculum of FIGS. 2-5(b), including the illumination assembly.

As shown in FIGS. 5(*a*) and 5(*b*), 6 and 7, the illumination assembly 1100 is intended to be fitted within the enclosed cavity 1024 of the handle portion 1020 and more specifically into the open upper end 1028. The illumination assembly 1100 is defined by a housing 1104 (partially shown in these figures), as well an extending curved arm 1112 that retains a light source. According to this embodiment, the distal end 1116, FIG. 5(*b*), of the extending curved arm 1112 retains an LED (not shown). The extending curved arm 1112 is shaped and configured to be fitted onto a necked portion 1044 of the lower blade member 1004, which is intermediately disposed between the handle portion 1020 and the trough-shaped blade section 1016 of the lower blade member 1008. According to this embodiment, at least a portion of the lower blade member 1008 in the necked portion 1044 is recessed to receive a distal portion of the extending curved arm 1112 in order to improve and effectively direct illumination from the retained light source toward the distal end 1012 of the speculum 1000. As shown in FIGS. 5(*a*) and 5(*b*), the positioning of the illumination assembly 1100 within the speculum 1000 permits illumination to be directed toward the intended target, but does not interfere with viewing through the rear viewing aperture 1068.

Figure 7:
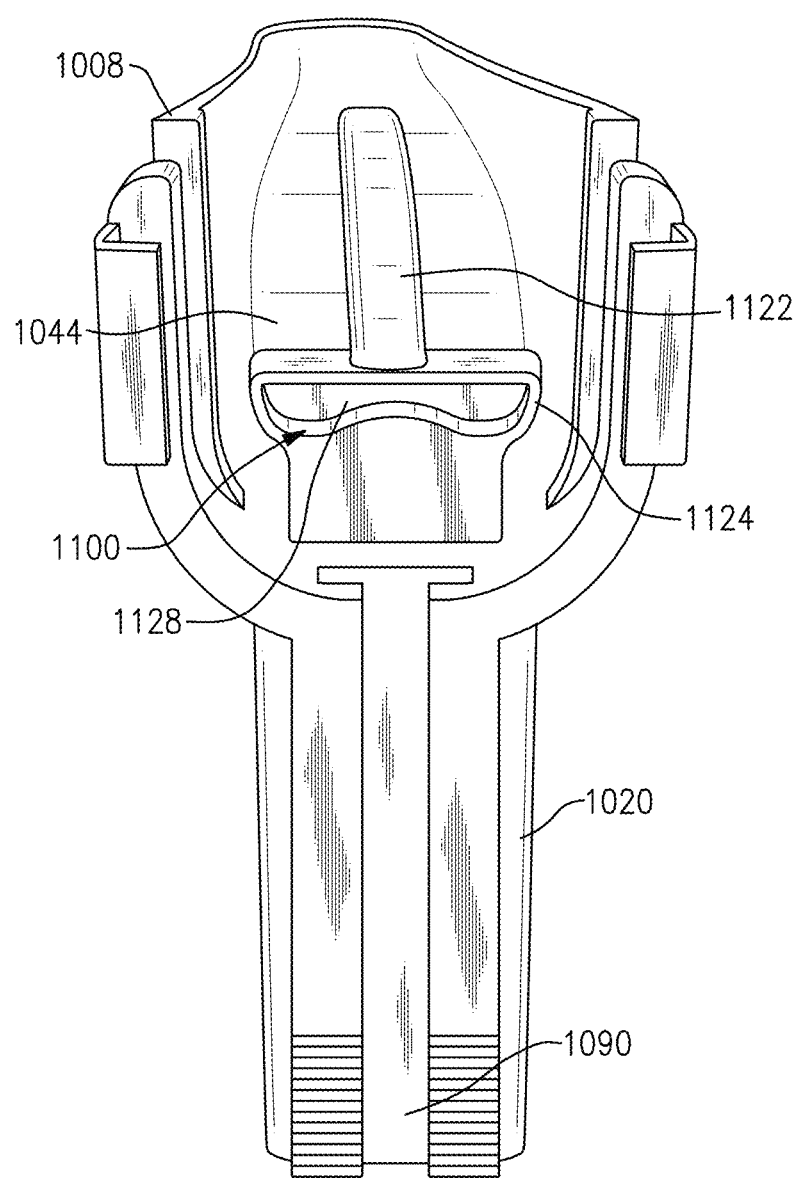
FIG. 7 is a rear facing view of the lower blade member and illumination assembly of FIG. 6.
Figure 9:
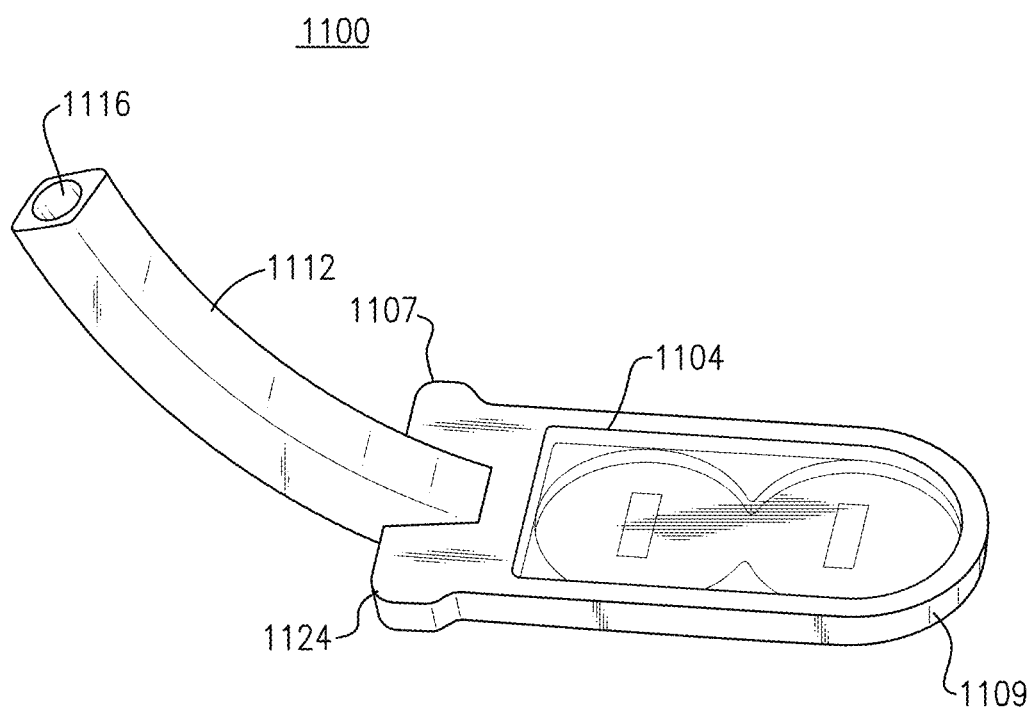
FIG. 9 is a front perspective view of the illumination assembly that is only partially shown in FIGS. 2 6 and 7.
Figure 10:
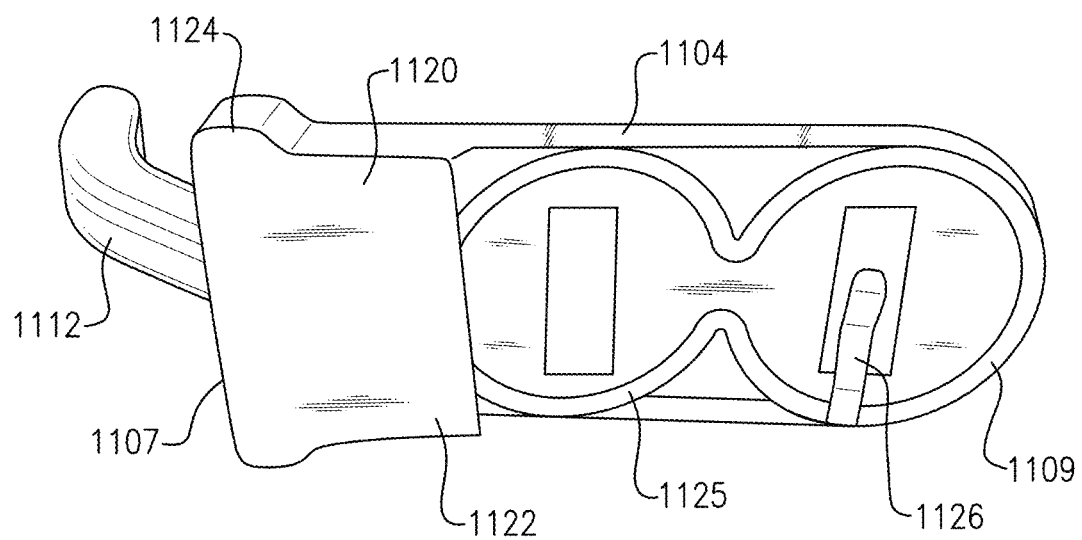
FIG. 10 is a rear perspective view of the illumination assembly of FIG. 9, with a portion of the cover broken away for clarity.

Further details of the illumination assembly 1100 are provided with reference to FIGS. 9 and 10. According to this embodiment, the illumination assembly 1100 includes the housing 1104, which is defined by an upper end 1107 and an opposing lower end 1109. The housing 1104 further includes an upper flanged section 1124 having a width that is larger than the width of the open upper end 1028 of the enclosed receiving cavity 1024 of the handle portion 1020, as shown in FIGS. 5 and 7. The upper end 1107 of the housing 1104 supports the extending curved arm 1112, which as noted retains an LED (not shown) at a distal end 1116 of the arm 1112. According to this embodiment, the curved arm 1112 is integral to the housing 1104 with the housing 1104 and extending arm 1112 being formed from a moldable plastic material, such as polyethylene (PETE) or polypropylene. It will be understood, however, that the extending arm 1112 can be alternatively and separately attached to the upper end 1107 of the housing 1104 by suitable techniques such as adhesives, welding, or fasteners.

The housing 1104 is defined by an interior that retains at least one battery (not shown). According to this embodiment, a pair of batteries such as Panasonic CR 2032 lithium coin batteries (+3 volts) are retained in side by side relation in adjacently spaced retaining peripheral slots 1125 integrally provided on an inner surface of the housing 1104. An electrical contact 1126, configured within the interior of the housing 1104, includes a first end arranged to engage the retained batteries, wherein the electrical contact 1126 extends along the length of the housing 1104 and into the interior of the curved arm 1112 with a second end of the electrical contact 1126 being arranged to engage the distally retained LED (not shown).

The housing 1104 further includes a cover 1120, which according to this embodiment includes an intermediate hinge 1122 disposed adjacent the upper end 1107 of the housing 1104. Though not shown, the housing 1104 can further include at least one and preferably two or more frangible tabs or similar features to secure the housing 1104 within the enclosed cavity 1024 of the handle portion 1020. Removal of the housing 1104 by pulling the assembly 1100 from the enclosed cavity 1024 breaks or otherwise disables the frangible tabs and prevents the illuminator housing 1104 from being reinstalled into the receiving cavity 1024. According to this embodiment, a recessed portion 1128, FIG. 7, of the upper flanged section 1124 assists in gripping the illumination assembly 1100 to enable permanent removal of the illumination assembly 1100 from the speculum 1000.

In use, the illumination assembly 1100 is disposed within the open upper end 1028 of the receiving cavity 1020 of the speculum 1000 with the extending curved arm 1112 being supported by the necked portion 1044 of the lower blade member 1008. The upper flanged portion 1024 prevents the housing 1104 from being advanced too far into the receiving cavity 1020 or falling through the cavity 1020, the housing 1104 being guided by the rails 1036. The frangible tabs (not shown) secure the illumination assembly 1100 in place.

Preferably, the housing 1104 is fully enclosed with the exception of a slot formed at the lower end 1109 that permits the passage of an extending tab member 1150, partially shown in FIG. 4(*a*). The tab member 1150 is made from an electrically inert material, such as plastic, and includes a distal portion disposed within the interior of the housing 1104. More specifically, the distal portion is positioned between the end of the electrical contact 1126 and the retained battery. The extending tab member 1150 includes a proximal end, the latter extending outwardly of the open lower end 1032 of the handle portion 1020. When the proximal end is pulled by a user and the tab member 1150 is removed from the housing 1104, engagement is created between the contained batteries and the first end of the electrical contact 1126, energizing the supported LED in the extending curved arm 1112. Illumination is directed toward the distal end 1012 of the speculum 1000 as the recess formed in the necked portion 1044 of the lower blade member 1008 assists in maximizing uniform distribution of light emitted by the LED.

Following its intended use the speculum 1000, including the illumination assembly 1100, can be disposed of for recycling. As noted and due to various environmental regulations and standards, the batteries should first be separated from the illumination assembly 1100. According to this described embodiment, there are two (2) techniques available for removing the contained batteries. First, the illumination assembly 1100 can be removed from the receiving cavity 1020 by gripping the upper flanged portion 1024 of the housing 1104 and extracting the assembly 1100 from the handle portion 1020. In so doing, the frangible tab features are disabled as a result of removing the housing 1104 from the open upper end 1028 of the receiving cavity 1024. The hinged cover 1120 can then be opened and the batteries can be removed from the retaining slots 1168.

According to a second technique, the batteries can be removed from the housing 1104 without first removing the illumination assembly 1100 from the speculum 1000. A tool (not shown) can be extended upwardly into the receiving cavity 1020 through the open lower end 1032 of the handle portion 1020 and more specifically into the open slot formed at the lower end 1109 of the housing 1104. The tool is shaped to pry open the hinged cover 1120, which drops the batteries which are vertically arranged, through the open lower end 1032 of the handle portion 1020. The speculum 1000 and illumination assembly 1100 can then be disposed of for purposes of recycling, without requiring further disassembly.

Figure 11:
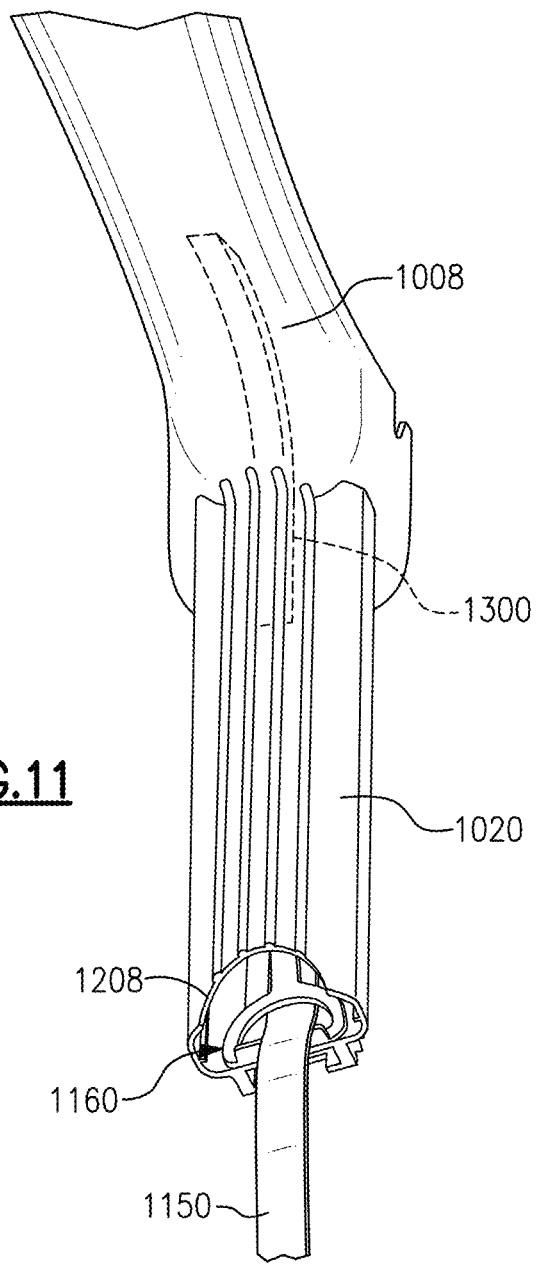
FIG. 11 is a bottom perspective view of a vaginal speculum in accordance with other aspects of the invention.
Figure 12:
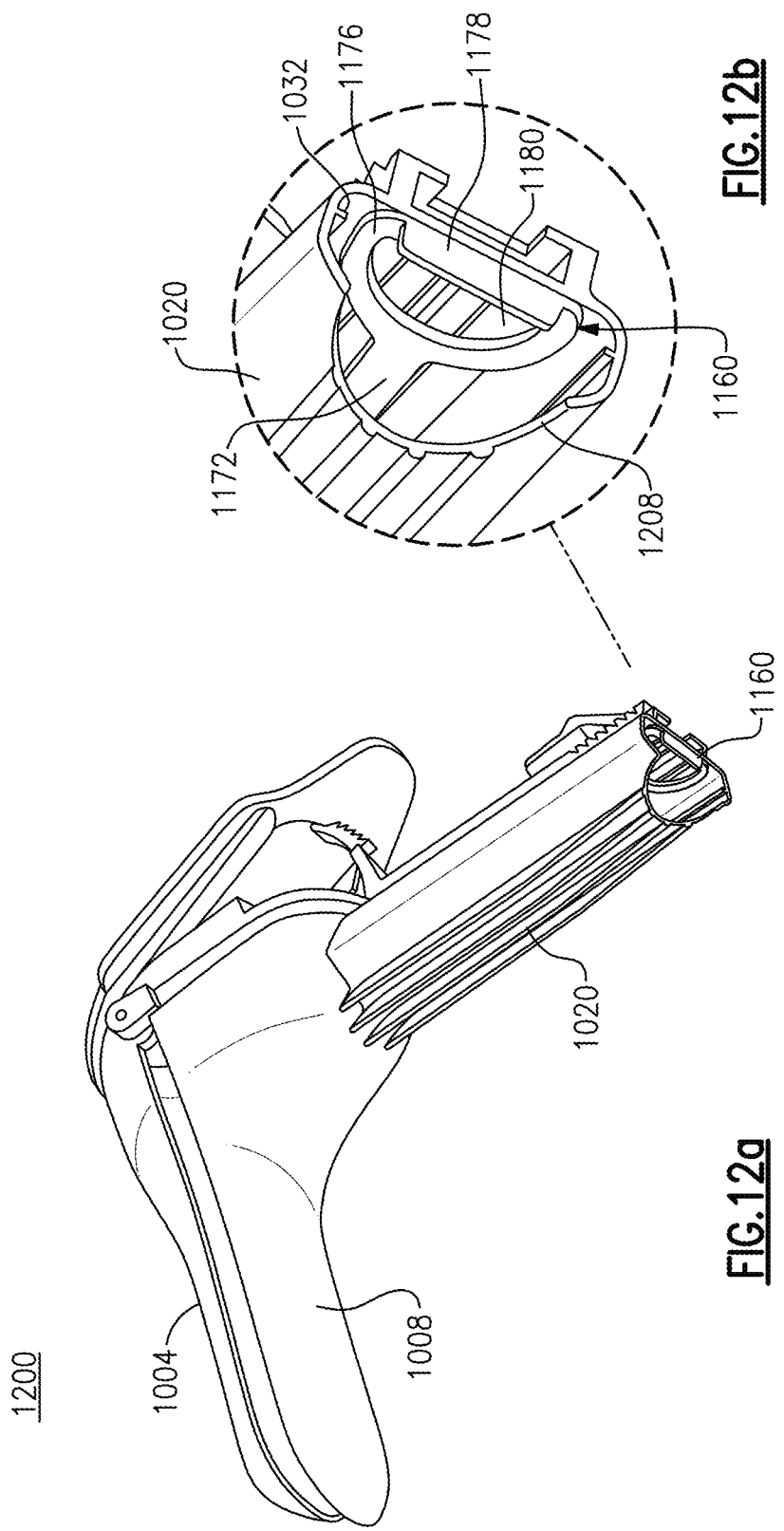
FIG. 12(a) is a bottom perspective view of the vaginal speculum of FIG. 11.
FIG. 12(b) is an enlarged view of the lower open end of the handle portion of the speculum of FIG. 12(a), partially depicting a battery release member.
Figure 13:
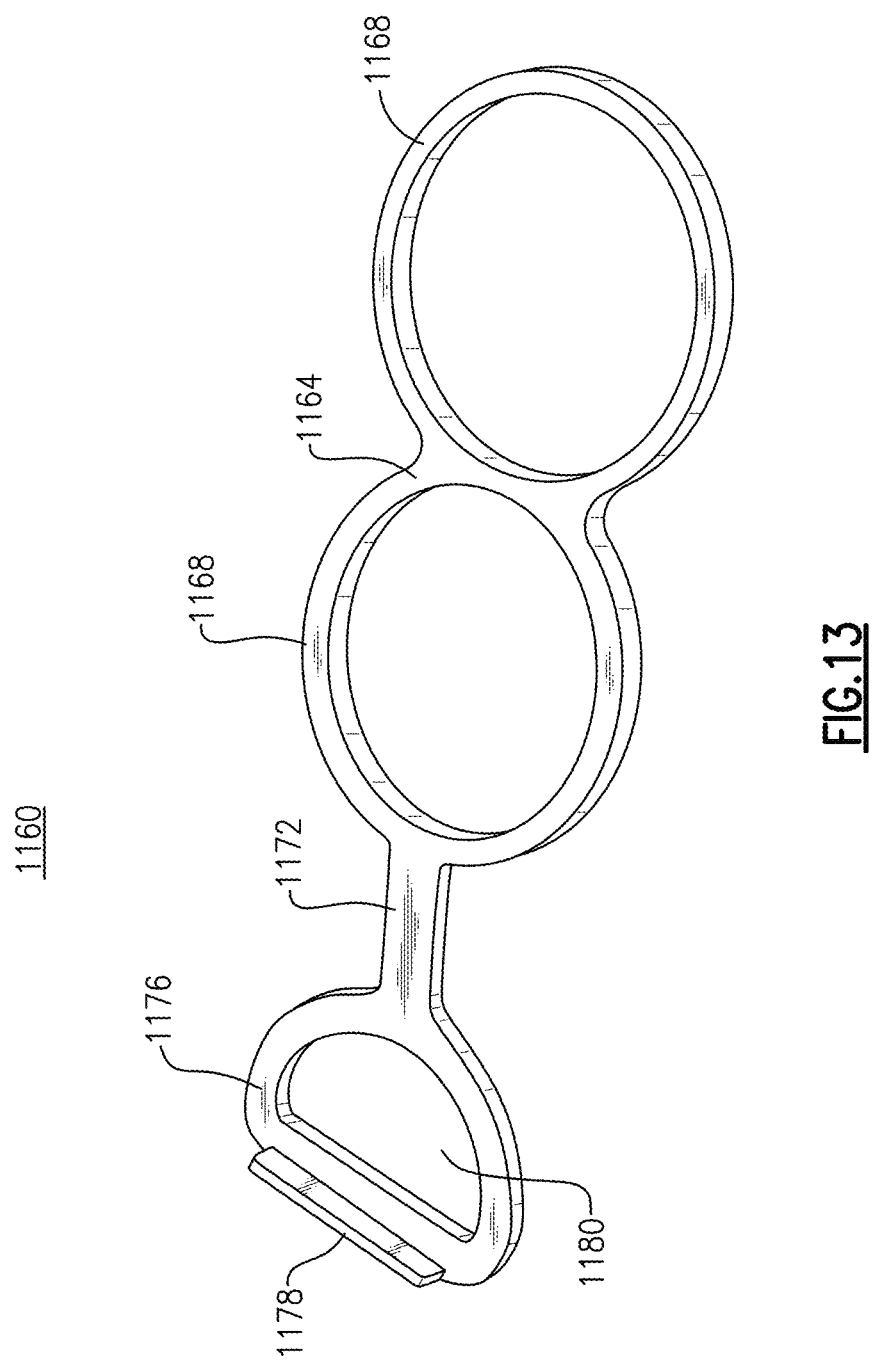
FIG. 13 is a perspective view of the battery release member of FIG. 12(b)

A further variation of a speculum 1200 having an integrated illumination assembly 1300 is shown with reference to FIGS. 11-13. For purposes of this discussion, similar parts are labeled with the same reference numerals for the sake of clarity. According to this version, the lower open end 1032 of the handle portion 1020 is recessed along one wall 1208 of the handle portion 1020 to permit finger access to a battery release member 1160, the latter extending downwardly from the lower end 1109, FIG. 10, of the housing 1104, FIG. 10, of the illumination assembly 1300, in addition to the extending tab member 1150. According to this embodiment and in lieu of a separate tool, the battery release member 1060 of the illumination assembly 1300 can be pulled entirely from the housing 1104, and more specifically the lower end 1109.

With reference to FIG. 13, the battery release member 1160 according to this embodiment is defined by a single component that includes a battery engagement portion 1164 at its distal end, which includes a pair of interconnected loops 1168. The battery engagement portion 1164 is sized to fit within the interior of the housing 1104 and the loops 1168 are each sized to peripherally cover one of the retained batteries (not shown). An intermediate planar portion 1172 of the battery release member 1160 extends to a proximal or user engagement end 1176 that extends proximate to the recess 1208 at the lower end of the handle portion 1020. According to this described embodiment, the user engagement end 1176 includes a loop 1180 that is appropriately sized to permit an extending proximal end of the releasable tab member 1150 to extend therethrough as well as a guide tab 1178. In this version, the extending proximal end of the releasable tab member 1150 is caused to extend over the guide tab 1178 at an acute angle relative to the handle portion 1020, as shown in FIG. 11.

The speculum 1200 and illumination assembly 1300 are otherwise no different structurally than the previously described versions 1000 and 1100, respectively. When the illumination assembly 1100 is mounted within the enclosed cavity 1024 of the handle portion 1020, the user engagement end 1176 of the battery release member 1160 is accessible from the open lower end 1032 of the handle portion 1020 via the recess 1208.

As in the preceding, the releasable tab member 1150 extends downwardly from the interior of the housing 1104 such that the proximal end of the tab member 1150 can be accessed from the open lower end 1032 of the receiving cavity 1024 of the handle portion 1020, as shown in FIG. 11. When the tab portion 1150 is pulled from the housing 1104, the electrical contact 1126, FIG. 10, is caused to engage the contained batteries and energize the retained LED. The releasable tab member 1150 is pulled from the speculum 1200 while the battery release member 1160 remains in place.

Following examination, the batteries can be removed by accessing the guide tab 1178 and pulling the user engagement end 1176 of the battery release member 1160. This pulling action withdraws the battery release member 1160, as well as the contained batteries, which drop from the lower end 1109 of the housing 1104 through the open lower end 1032 of the handle portion 1020. Alternatively and as previously described, the user can separately remove the illumination assembly 1300 by engaging the recessed portion 1128 of the upper flanged section 1124 to pull the illumination assembly 1300 from the handle portion 1020 of the speculum 1000. Once removed, the hinged cover 1120 can be opened and the batteries can be removed prior to recycling the illumination assembly 1300.

As noted, the herein described illumination assembly (whether 1100 or 1300) can be used in conjunction with other hand-held medical instruments or devices other than a vaginal speculum, the latter being merely an embodiment. For example and with reference to FIGS. 14 and 15, an illumination assembly 1100 is depicted for use with a laryngoscope 1500, the latter instrument being used typically for examining the throat of a patient. The laryngoscope 1500 according to this embodiment is defined by a handle or handle portion 1508 that downwardly extends from the proximal end of a single curved blade 1514, the latter being configured and shaped for examining the throat of a patient (not shown). The handle 1508 is shaped and configured to permit one-handed operation of the instrument 1500 by a practitioner or care provider. The handle 1508 and blade 1514 according to this version are made as a unitary component made from a recyclable plastic, such as polyethylene.

The salient features of the illumination assembly 1100 are as previously described. That is and as partially shown in FIG. 14, the illumination assembly 1100 is defined by a housing 1104 having a width dimension at the top or upper portion of the housing 1104 that is wider than a cavity formed in the top or upper portion of the unitary handle 1508. A curved arm 1112 extends outwardly from the housing 1104, the latter being shaped and configured to extend partially within the confines of the curved blade 1514. At least one LED 1190 mounted at the distal end of the curved arm 1112 is electrically coupled to a set of compact batteries (not shown) retained within the housing 1104 of the illumination assembly 1100. According to at least one version, both the illumination assembly 1100 and the laryngoscope 1500 can be made from the same recyclable plastic material.

According to this embodiment, the output of the LED 1190 is optically coupled via a guide 1550, the latter being retained within a pocket 1558 formed in the curved blade 1514 to direct light to the patient (not shown) being examined. The guide 1550 according to this embodiment is defined by a substantially conical shape and made from a light transmissive material, such as an acrylic, that is formed with a diffused end. The guide 1550 is configured to effectively direct emitted light from the LED 1190 to the distal end of the blade 1514 and subsequently the throat of the patient.

Figure 14:
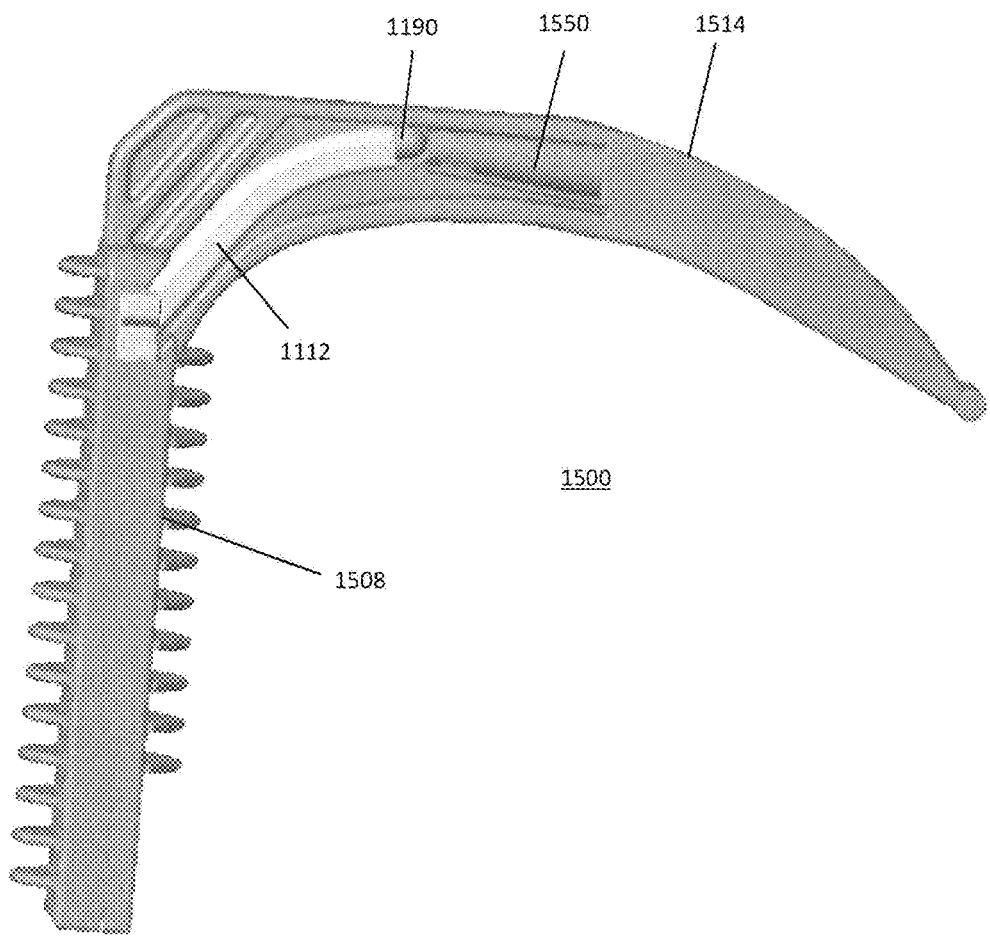
FIG. 14 is a side perspective view of another handheld medical device equipped with an illumination assembly in accordance with aspects of the present invention.
Figure 15:
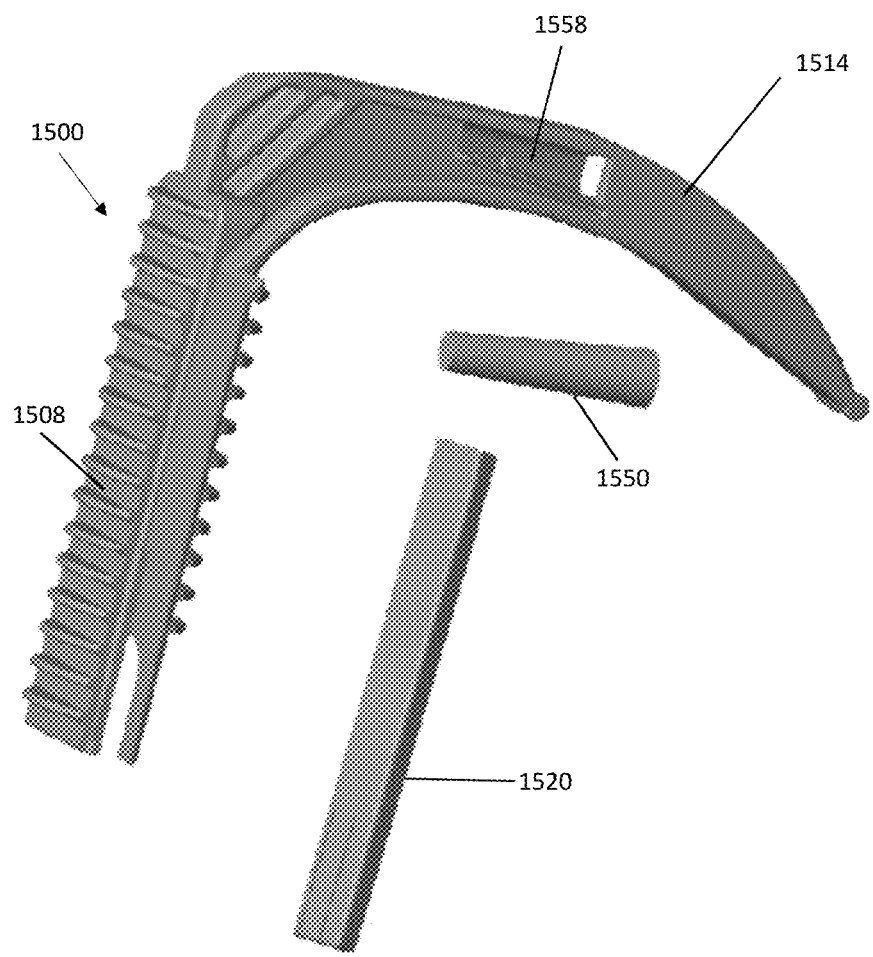
FIG. 15 is a partially exploded view of the handheld medical device of FIG. 14.
Figure 16:
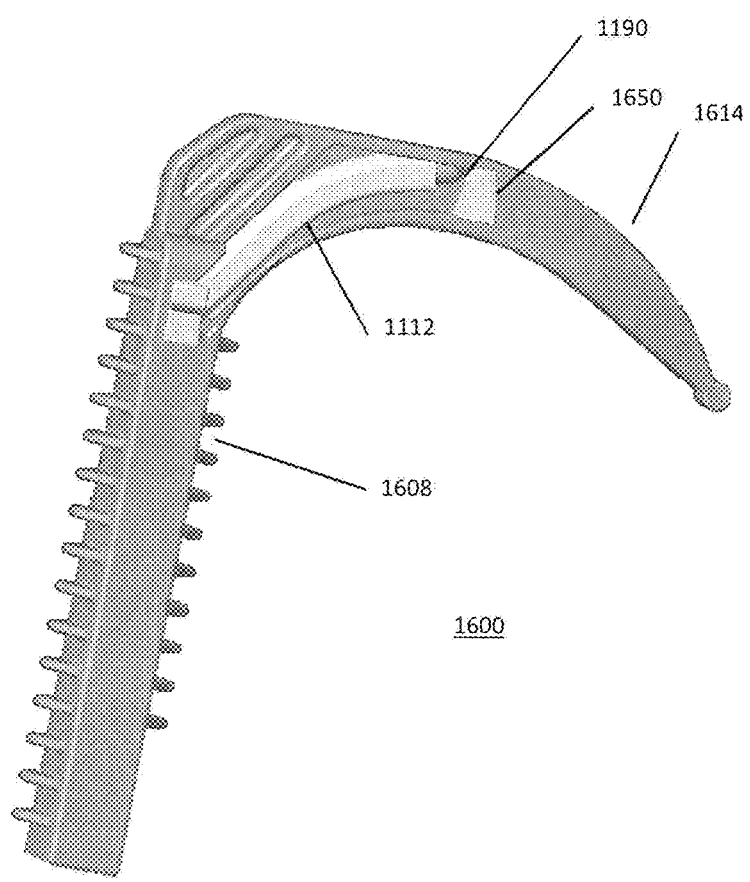
FIG. 16 is a side perspective view of another handheld medical device equipped with an illumination assembly in accordance with aspects of the present invention.
Figure 17:
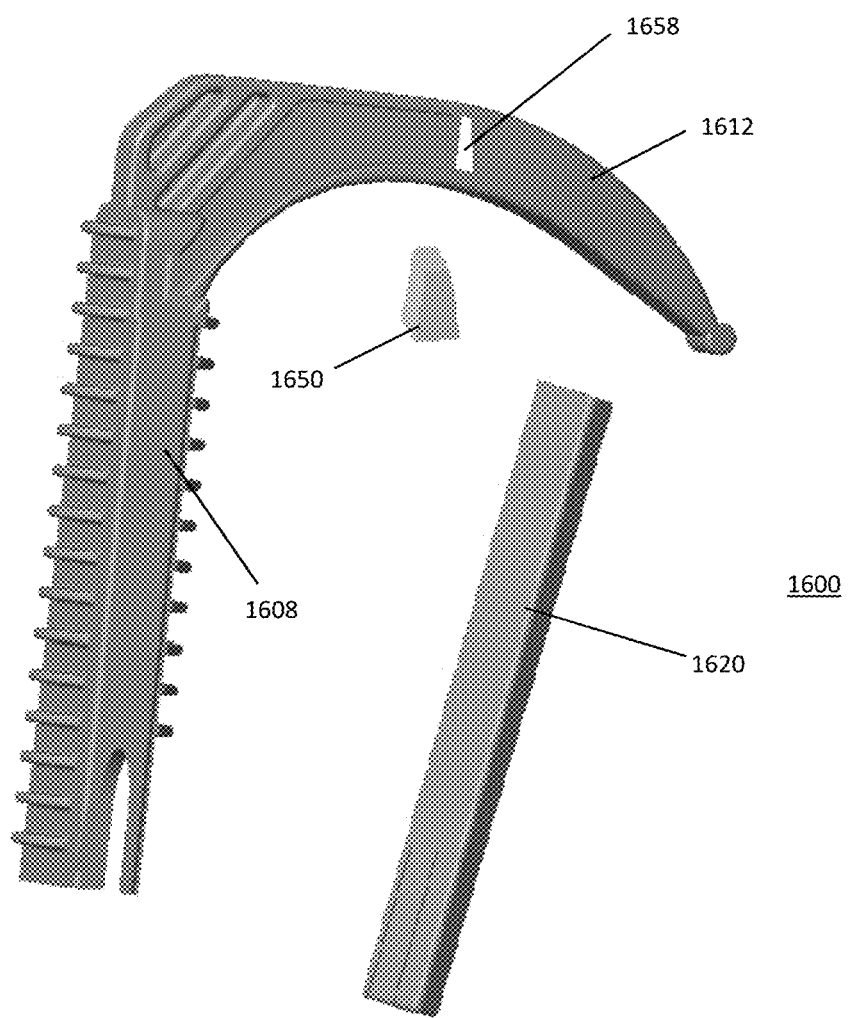
FIG. 17 is a partially exploded view of the handheld medical device of FIG. 16.

FIGS. 14 and 15 illustrates a laryngoscope 1500 having an adult (large) laryngoscope blade 1514. A similar version, shown in FIGS. 16 and 17, depicts a laryngoscope 1600 having a smaller adult laryngoscope blade 1614, which is inherently narrower dimensionally. In this latter version and in lieu of a conical guide, the LED 1190 of the contained illumination assembly 1100 is optically coupled with a guide in the form of a prism 1650. The prism 1650 is made from a light transmissive material that is configured and positioned within a pocket or cavity 1658 formed in the blade 1614 of the laryngoscope 1600 in order to effectively direct emitted light from the contained illumination assembly 1100, and more specifically the LED 1190.

In each of the versions depicted in FIGS. 14-17 and as in the prior embodiments described above, the illumination assembly 1100 (or 1300 or variants) is preferably configured for energization of the LED 1190 using an extending tab member that is accessible via an open end of the handle 1508, 1608 of the laryngoscope 1500, 1600. Removal of the contained batteries can be realized using a tool (not shown) configured to open a hinged cover of the housing 1104 or alternatively via a battery release member (not shown), as previously described, which can be pulled to enable the contained batteries to drop through an open end at the bottom of the formed cavity in the handle of the instrument 1500, 1600. Alternatively, the illumination assembly 1100 can be separately removed from the handle of the laryngoscope and the batteries can be removed by accessing the hinged cover of the housing 1104.

According to this version, the instrument handle 1508, 1608 can further or alternatively include a frangible side cover 1520, 1620 to permit removal of the illumination assembly 1100 in order to remove the retained batteries from the housing 1104. Preferably, removal of the side cover 1520, 1620 limits the structural capability of the instrument handle 1508, 1608 for continued use as an instrument handle, thereby preventing any subsequent reinstallation of the illumination assembly 1100. In each of the above embodiments, the batteries can be removed separately prior to recycling of the instrument 1500, 1600, including the illumination assembly 1100.

Figure 18:
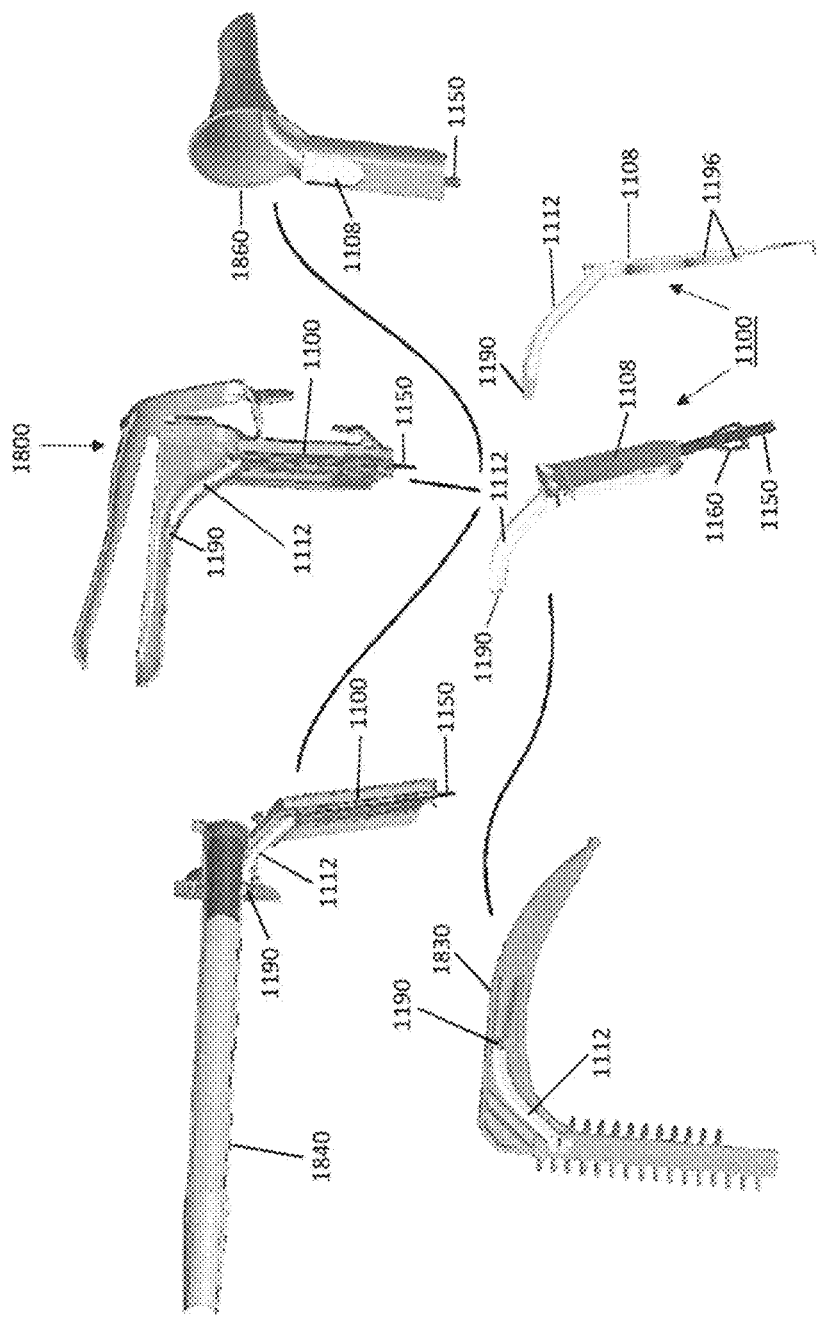
FIG. 18 depicts an illumination assembly in accordance with aspects of the invention as used in conjunction with a suite of disparate and recyclable handheld medical devices.

FIG. 18 depicts the further use of an illumination assembly 1100 in conjunction with a number of disparate recyclable medical devices. Though the assembly 1100 is shown here, it will be understood that other variants can be utilized for this purpose. As shown, the illumination assembly 1100 includes a housing 1108, as well as a curved arm 1112 extending from an upper end of the housing 1108 that retains an LED 1190 at its distal end, the LED 1190 being coupled electrically to a set of batteries 1196 that are retained in the housing 1108. The housing 1108 can include a hinged cover, as well as a lower or bottom extending tab portion or member 1150 that can be used as a switch to energize the LED 1190 when pulled by a user. A battery release member 1160, as described above, is also provided to enable the contained batteries 1196 to be withdrawn from the housing 1104 in a manner, as previously described. As shown, the illumination assembly 1100 can be integrated within a vaginal speculum 1800, a laryngoscope 1830, in addition to a sigmoidscope 1840, and an anoscope 1860, each of the foregoing instruments being typically configured for examining a different medical target. This depicted incorporation enables a suite of hand-held medical instruments to be reserved for single use or single patient use and further enables recyclability. Still other hand-held medical devices, such as rhinoscopes and skin measuring microscopes, among others, can be similarly equipped.

PARTS LIST—FIGS. 1-18

100 vaginal speculum
104 first or top blade member
108 second or bottom blade member
112 distal end, blade members
116 proximal end, blade members
118 trough-shaped blade portion
120 handle portion
126 enclosed receiving cavity
128 open lower end
132 closed upper end
136 curved light pipe
138 proximal end, light pipe
140 distal end, light pipe
144 necked portion
148 centering fingers
152 lens
160 illuminator, portable
162 housing, illuminator
163 upper end
164 upper portion, illuminator
165 slide switch, exterior
166 lower portion, illuminator
168 charging contact, battery
170 lever portion
174 viewing aperture
176 lower tab
178 slot, tab
180 yoke
182 yoke portion
184 upwardly extending spaced arms
186 slide member
190 vertical slot
194 lower locking member
196 spaced teeth
198 arcuate pawl arm
199 teeth, ratchet
202 recessed portion
1000 speculum
1004 first or upper blade member
1008 second or lower blade member
1012 distal end
1016 trough-shaped blade portion
1018 proximal end
1020 handle portion
1024 axial cavity, enclosed
1028 open upper end
1032 open lower end
1036 guide rails
1044 necked portion
1056 recessed portion
1060 channels
1062 guiding features
1064 lever portion
1068 viewing aperture
1070 lower tab
1074 slot
1080 yoke
1084 yoke portion
1085 upwardly extending arms
1086 slide member
1090 vertical slot
1094 lower locking member
1096 teeth, spaced
1098 arcuate pawl arm
1099 ratchet teeth
1100 illuminator assembly
1104 housing
1107 upper end, housing
1109 lower end, housing 1112 curved arm
1116 distal end
1120 cover
1122 hinge, intermediate
1124 upper flanged section, housing
1125 retaining peripheral slots
1126 electrical contact
1128 recessed portion
1150 releasable tab portion
1160 battery release member
1164 battery engagement or support portion
1168 loops, interconnected
1172 outwardly extending portion
1176 user engagement end
1178 guide tab
1180 loop
1190 LED
1196 batteries
1200 speculum
1208 access slot
1300 illumination assembly
1500 laryngoscope
1508 handle
1514 blade
1520 side cover
1550 guide
1558 pocket
1600 laryngoscope
1608 handle
1614 blade
1620 side cover
1650 prism
1658 pocket or cavity
1800 vaginal speculum
1830 laryngoscope
1840 sigmoidoscope
1860 anoscope It will be readily apparent that the foregoing description is exemplary of the inventive concepts. These and other variations and modifications are possible, as defined by the following claims.

We claim:

1. A vaginal speculum comprising:
a first blade member;
a second blade member;
a handle portion downwardly extending from the second blade member, the handle portion having an axial cavity that is fully enclosed with the exception of open and opposing upper and lower ends; and
an illumination assembly that is releasably engageable with and removable from the handle portion, the illumination assembly comprising:
an assembly housing including an enclosed interior battery compartment;
at least one battery disposed within the enclosed interior battery compartment; and
an LED disposed at a distal end of an integral curved arm extending from an upper end of the assembly housing and coupled to the at least one battery, the assembly housing being releasably mounted within and releasably removable from the axial cavity of the handle portion through the open upper end with the integral curved arm of the illumination assembly being supported by the second blade member and configured to provide direct illumination to a medical target, the assembly housing further comprising:
the upper end and a lower end, the upper end having a flanged section that is sized larger than the open upper end of the handle portion, and
the lower end having the enclosed interior battery compartment being fully retained within the enclosed axial cavity of the handle portion, wherein the flanged section provides a mechanical stop to prevent over insertion of the assembly housing into the upper open end of the handle portion, the flanged section being recessed to enable gripping of the assembly housing to facilitate removal from the open upper end of the handle portion.

2. The speculum according to claim 1, in which one of the assembly housing and the enclosed axial cavity of the handle portion further comprises at least one frangible tab such that removal of the assembly housing from the open upper end of the handle portion breaks the at least one frangible tab to render the speculum and the illumination assembly from any reuse.

3. The speculum according to claim 1, in which the illumination assembly further comprises a tab portion extending outwardly from the assembly housing, wherein the tab portion is releasable from the assembly housing to cause energization of the LED, the tab portion being accessible through the open lower end of the handle portion.

4. The speculum according to claim 1, in which the second blade member includes a recess sized to receive at least the distal end of the extending curved arm.

5. The speculum according to claim 1, in which the assembly housing includes a hinged cover and in which the lower end of the assembly housing is configured within the enclosed axial cavity of the handle portion such that the hinged cover can be opened to enable the least one battery to be removed from the battery compartment while the lower end of the assembly housing remains mounted within the enclosed axial cavity.

6. The speculum according to claim 5, wherein the hinged cover is configured to be opened by a tool engaged within the open lower end of the handle portion.

7. The speculum according to claim 6, including a battery release member outwardly extending from the lower end of the assembly housing, wherein a first end of the battery release member within the assembly housing includes at least one battery retaining feature and a second opposing end of the battery release member is accessible from the lower open end of the handle portion.

8. The speculum according to claim 7, in which the battery release member is releasably attached to the assembly housing.

9. The speculum according to claim 1, in which the extending curved arm is made of an opaque plastic material.

10. A vaginal speculum comprising:
a first blade member;
a second blade member;
a handle portion downwardly extending from the second blade member, the handle portion having an axial cavity that is fully enclosed with the exception of open and opposing upper and lower ends; and
an illumination assembly that is releasably engageable with and removable from the open upper end of the handle portion, the illumination assembly comprising:
an assembly housing including an upper portion and a lower portion, the lower portion including an enclosed interior battery compartment retaining at least one battery; and the upper portion of the assembly housing including a curved arm extending above the open upper end of the axial cavity and retaining an LED at a distal end that is coupled to the at least one battery, wherein the enclosed battery compartment includes a hinged cover, wherein the at least one battery can be removed from the enclosed battery compartment either while the lower portion of the assembly housing is still retained within the axial cavity of the handle portion or after the assembly housing has been removed from the open upper end of the handle portion.

11. The speculum according to claim 10, in which the illumination assembly further comprises a tab portion extending outwardly from the assembly housing, wherein the tab portion is releasable from the assembly housing to cause energization of the LED, the tab portion being accessible through the open lower end of the handle portion.

12. The speculum according to claim 10, wherein the hinged cover is configured to be opened by a tool engaged within the open lower end of the handle portion.

13. The speculum according to claim 12, including a battery release member outwardly extending from a lower end of the assembly housing, wherein a first end of the battery release member within the assembly housing includes at least one battery retaining feature and a second opposing end of the battery release member is accessible from the lower open end of the handle portion.

14. The speculum according to claim 13, in which the battery release member is releasably attached to the assembly housing.

15. The speculum according to claim 10, in which one of the assembly housing and the enclosed axial cavity of the handle portion further comprises at least one frangible tab such that removal of the assembly housing from the open upper end of the handle portion breaks the at least one frangible tab to render the speculum and the illumination assembly from reuse.

\* \* \* \* \*